US012734049B2

(12) United States Patent
Huang et al.

(10) Patent No.: US 12,734,049 B2
(45) Date of Patent: Sep. 15, 2026

(54) SYSTEMS AND METHODS FOR REINFORCEMENT LEARNING CONTROL OF A POWERED PROSTHESIS

(71) Applicants: North Carolina State University, Raleigh, NC (US); ARIZONA BOARD OF REGENTS ON BEHALF OF ARIZONA STATE UNIVERSITY, Scottsdale, AZ (US)

(72) Inventors: He Huang, Cary, NC (US); Yue Wen, Raleigh, NC (US); Jennie Si, Phoenix, AZ (US); Xiang Gao, Tempe, AZ (US); Minhan Li, Raleigh, NC (US)

(73) Assignees: North Carolina State University, Raleigh, NC (US); ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 1031 days.

(21) Appl. No.: 17/792,695

(22) PCT Filed: Nov. 16, 2020

(86) PCT No.: PCT/US2020/060703

§ 371 (c)(1),
(2) Date: Jul. 13, 2022

(87) PCT Pub. No.: WO2021/145948

PCT Pub. Date: Jul. 22, 2021

(65) Prior Publication Data

US 2023/0066952 A1 Mar. 2, 2023

Related U.S. Application Data

(60) Provisional application No. 62/961,289, filed on Jan. 15, 2020.

(51) Int. Cl.
*A61F 2/68* (2006.01)
*A61F 2/70* (2006.01)
*A61F 2/76* (2006.01)

(52) U.S. Cl.
CPC .......... *A61F 2/68* (2013.01); *A61F 2002/701* (2013.01); *A61F 2002/7625* (2013.01)

(58) Field of Classification Search
CPC .......................................................... A61F 2/68
See application file for complete search history.

(56) References Cited

U.S. PATENT DOCUMENTS 8,403,997 B2 * 3/2013 Sykes .................... A61B 5/112 623/24
8,915,968 B2 * 12/2014 Langlois .................. A61F 2/70 623/24

(Continued)

FOREIGN PATENT DOCUMENTS

CN 113780223 A * 12/2021 ............. G06N 3/047
WO WO-2007110585 A2 * 10/2007 ............. A61B 5/112

(Continued)

OTHER PUBLICATIONS

International Search Report and Written Opinion issued for Application No. PCT/US2020/060703, dated Feb. 12, 2021, 10 pages.

(Continued)

*Primary Examiner* — Jacqueline Woznicki
(74) *Attorney, Agent, or Firm* — Meunier Carlin & Curfman LLC

(57) ABSTRACT

Systems and methods for tuning a powered prosthesis are described herein. A system includes a powered prosthesis including a joint, a motor mechanically coupled to the joint, a plurality of sensors, a finite state machine, and an impedance controller. The sensors are configured to measure a plurality of gait parameters, and the finite state machine is configured to determine a gait cycle state. The impedance (Continued)

controller is configured to output a control signal for adjusting a torque of the motor, where the torque is adjusted as a function of the measured gait parameters and a plurality of impedance control parameters, and where the impedance control parameters are dependent on the gait cycle state. The system also includes a reinforcement learning controller operably connected to the powered prosthesis. The reinforcement learning controller is configured to tune the impedance control parameters to achieve a target gait characteristic using a training data set.

25 Claims, 18 Drawing Sheets

(56) References Cited

U.S. PATENT DOCUMENTS

| | | | | |
|---|---|---|---|---|
| 9,180,025 | B2 * | 11/2015 | Goldfarb | A61F 2/60 |
| 9,221,177 | B2 * | 12/2015 | Herr | B25J 9/1694 |
| 9,289,315 | B2 * | 3/2016 | Goldfarb | A61F 2/66 |
| 9,333,097 | B2 * | 5/2016 | Herr | A61F 2/604 |
| 10,335,294 | B2 | 7/2019 | Huang et al. | |
| 2005/0283257 | A1 * | 12/2005 | Bisbee, III | A61F 2/70 623/44 |
| 2011/0125290 | A1 * | 5/2011 | Langlois | A61F 2/70 623/27 |
| 2012/0083901 | A1 * | 4/2012 | Langlois | A61F 2/70 623/24 |
| 2013/0261766 | A1 * | 10/2013 | Langlois | A61F 2/70 623/33 |
| 2013/0268090 | A1 * | 10/2013 | Goldfarb | A61F 2/70 623/24 |
| 2013/0274894 | A1 * | 10/2013 | Goldfarb | A61F 2/70 623/24 |
| 2016/0242936 | A1 | 8/2016 | Goldfarb et al. | |
| 2017/0119551 | A1 | 5/2017 | Huang et al. | |
| 2018/0235781 | A1 * | 8/2018 | Langlois | A61F 2/60 |
| 2022/0198253 | A1 * | 6/2022 | Benosman | G06F 18/214 |
| 2022/0378588 | A1 * | 12/2022 | Einarsson | A61F 2/70 |
| 2023/0066952 | A1 * | 3/2023 | Huang | A61F 2/68 |
| 2023/0201010 | A1 * | 6/2023 | Einarsson | A61F 2/64 623/24 |

FOREIGN PATENT DOCUMENTS

| | | | | |
|---|---|---|---|---|
| WO | WO-2008032967 | A1 * | 3/2008 | A61H 3/008 |
| WO | WO-2021145948 | A1 * | 7/2021 | A61F 2/76 |
| WO | WO-2024178129 | A1 * | 8/2024 | A61F 2/70 |

OTHER PUBLICATIONS

A. Brandt, Y. Wen, M. Liu, J. Stallings, and H. Huang, "Interactions Between Transfemoral Amputees and a Powered Knee Prosthesis During Load Carriage," Sci. Rep., vol. 7, No. 1, p. 14480, Nov. 2017.

A. H. Shultz and M. Goldfarb, "A Unified Controller for Walking on Even and Uneven Terrain with a Powered Ankle Prosthesis," IEEE Trans. Neural Syst. Rehabil. Eng., vol. 26, No. 4, pp. 788-797, Feb. 2018.

A. M. Simon, K. a. Ingraham, N. P. Fey et al., "Configuring a powered knee and ankle prosthesis for transfemoral amputees within five specific ambulation modes," PLoS One, vol. 9, No. 6, p. e99387, Jun. 2014.

B. E. Lawson, H. A. Varol, A. Huff, E. Erdemir, and M. Goldfarb, "Control of stair ascent and descent with a powered transfemoral prosthesis," IEEE Trans. Neural Syst. Rehabil. Eng., vol. 21, No. 3, pp. 466-473, May 2013.

B. E. Lawson, H. A. Varol, and M. Goldfarb, "Standing stability enhancement with an intelligent powered transfemoral prosthesis," IEEE Trans. Biomed. Eng., vol. 58, No. 9, pp. 2617-2624, Jun. 2011.

C. Lu, J. Si, and X. Xie, "Direct Heuristic Dynamic Programming for Damping Oscillations in a Large Power System," IEEE Trans. Syst. Man, Cybern. Part B Cybern., vol. 38, No. 4, pp. 1008-1013, Aug. 2008.

D. Quintero, D. J. Villarreal, D. J. Lambert, S. Kapp, and R. D. Gregg, "Continuous-Phase Control of a Powered Knee-Ankle Prosthesis: Amputee Experiments Across Speeds and Inclines," IEEE Trans. Robot., vol. 34, No. 3, pp. 686-701, Feb. 2018.

D. V. Prokhorov and D. C. Wunsch, "Adaptive critic designs," IEEE Trans. Neural Netw., vol. 8, No. 5, pp. 997-1007, Sep. 1997.

D. Vogt, S. Stepputtis, S. Grehl, B. Jung, and H. Ben Amor, "A system for learning continuous human-robot interactions from human-human demonstrations," in Proc.—IEEE Int. Conf. Robot. Autom., 2017.

D. Wang and D. Liu, "Learning and Guaranteed Cost Control With Event-Based Adaptive Critic Implementation," IEEE Trans. Neural Networks Learn. Syst., pp. 1-11, Apr. 2018.

D. Wang, H. He, and D. Liu, "Adaptive Critic Nonlinear Robust Control: A Survey," IEEE Trans. Cybern., vol. 47, No. 10, pp. 3429-3451, Oct. 2017.

D. Wang, H. He, X. Zhong, and D. Liu, "Event-Driven Nonlinear Discounted Optimal Regulation Involving a Power System Application," IEEE Trans. Ind. Electron., vol. 64, No. 10, pp. 8177-8186, Oct. 2017.

Ding, M. Kim, S. Kuindersma, and C. J. Walsh, "Human-in-the-loop optimization of hip assistance with a soft exosuit during walking," Sci. Rob., vol. 3, No. 15, Feb. 2018.

E. J. Rouse, L. J. Hargrove, E. J. Perreault, and T. a. Kuiken, "Estimation of human ankle impedance during the stance phase of walking," IEEE Trans. Neural Syst. Rehabil. Eng., vol. 22, No. 4, pp. 870-878, Jul. 2014.

E. J. Rouse, L. M. Mooney, and H. Herr, "Clutchable series-elastic actuator: Implications for prosthetic knee design," Int. J. Rob. Res., vol. 33, No. 13, pp. 1611-1625, Oct. 2014.

F. Liu, J. Sun, J. Si, W. Guo, and S. Mei, "A boundedness result for the direct heuristic dynamic programming," Neural Netw., vol. 32, No. Special Issue, pp. 229-235, Aug. 2012.

F. Sup, A. Bohara, and M. Goldfarb, "Design and control of a powered transfemoral prosthesis," Int. J. Rob. Res., vol. 27, No. 2, pp. 263-273, Feb. 2008.

F. Sup, H. A. Varol, J. Mitchell, T. J. Withrow, and M. Goldfarb, "Preliminary evaluations of a self-contained anthropomorphic transfemoral prosthesis," IEEE Asme Trans Mechatron. 2009; 14(6): 667-676.

H. Huang, D. L. Crouch, M. Liu, G. S. Sawicki, and D. Wang, "A Cyber Expert System for Auto-Tuning Powered Prosthesis Impedance Control Parameters," Ann. Biomed. Eng., vol. 44, No. 5, pp. 1613-1624, Sep. 2016.

H. Zhang, J. Zhang, G. H. Yang, and Y. Luo, "Leader-based optimal coordination control for the consensus problem of multiagent differential games via fuzzy adaptive dynamic programming," IEEE Trans. Fuzzy Syst., vol. 23, No. 1, pp. 152-163, Feb. 2015.

H. Zhang, L. Cui, X. Zhang, and Y. Luo, "Data-driven robust approximate optimal tracking control for unknown general nonlinear systems using adaptive dynamic programming method," IEEE Trans. Neural Netw., vol. 22, No. 12, pp. 2226-2236, Dec. 2011.

I. Mordatch, N. Mishra, C. Eppner, and P. Abbeel, "Combining model-based policy search with online model learning for control of physical humanoids," in IEEE Int. Conf. Robot. Autom., Stockholm, 2016, pp. 242-248.

J. K. Hitt, T. G. Sugar, M. Holgate, and R. Bellman, "An Active Foot-Ankle Prosthesis With Biomechanical Energy Regeneration," J. Med. Device., vol. 4, No. 1, p. 011003, Mar. 2010.

J. Peters and S. Schaal, "Reinforcement learning of motor skills with policy gradients," Neural Netw., vol. 21, No. 4, pp. 682-697, May 2008.

J. R Koller, D. H Gates, D. P Ferris, and C. David Remy, "'Body-in-the-Loop' Optimization of Assistive Robotic Devices: A Validation Study," in Robot. Sci. Syst. XII, Ann Arbor, Jun. 2016.

J. Si and Y. T. Wang, "On-line learning control by association and reinforcement," IEEE Trans. Neural Networks, vol. 12, No. 2, pp. 264-276, Mar. 2001.

(56) References Cited

OTHER PUBLICATIONS

J. Zhang, H. Zhang, and T. Feng, "Distributed Optimal Consensus Control for Nonlinear Multiagent System With Unknown Dynamic," IEEE Trans. Neural Networks Learn. Syst., vol. 29, No. 8, pp. 3339-3348, Aug. 2017.
J. Zhang, P. Fiers, K. A. Witte et al., "Human-in-the-loop optimization of exoskeleton assistance during walking," Science, vol. 356, No. 6344, pp. 1280-1284, Jun. 2017.
L. Ambrozic, M. Gorsic, J. Geeroms et al., "CYBERLEGs: A user-oriented robotic transfemoral prosthesis with whole-body awareness control," IEEE Robot. Autom. Mag., vol. 21, No. 4, pp. 82-93, Dec. 2014.
L. Yang, J. Si, K. S. Tsakalis, and A. A. Rodriguez, "Direct heuristic dynamic programming for nonlinear tracking control with filtered tracking error," IEEE Trans. Syst. Man, Cybern. Part B Cybern., vol. 39, No. 6, pp. 1617-1622, Dec. 2009.
Li, Minhan, et al. "Offline policy iteration based reinforcement learning controller for online robotic knee prosthesis parameter tuning." 2019 International conference on robotics and automation (ICRA). IEEE, 2019, 2831-2837.
M. F. Eilenberg, H. Geyer, and H. Herr, "Control of a powered ankle-foot prosthesis based on a neuromuscular model," IEEE Trans. Neural Syst. Rehabil. Eng., vol. 18, No. 2, pp. 164-173, Apr. 2010.
M. G. Lagoudakis and R. Parr, "Least-squares policy iteration," J. Mach. Learn. Res., vol. 4, pp. 1107-1149, Dec. 2003.
M. Grant and S. Boyd, "CVX: Matlab software for disciplined convex programming" http://cvxr.com/cvx, Mar. 2014.
M. I. Jordan and R. A. Jacobs, "Learning to control an unstable system with forward modeling," in Adv. Neural Inf. Process. Syst., D. S. Touretzky, Ed. Morgan-Kaufmann, 1990, pp. 324-331.
M. L. Handford, M. Srinivasan, M. Hulliger, and R. Zernicke, "Robotic lower limb prosthesis design through simultaneous computer optimizations of human and prosthesis costs," Sci. Rep., pp. 1-7, Feb. 2016.
M. Liu, F. Zhang, P. Datseris, and H. Huang, "Improving Finite State Impedance Control of Active-Transfemoral Prosthesis Using Dempster-Shafer Based State Transition Rules," J. Intell. Robot. Syst., vol. 76, No. 3, pp. 461-474, Dec. 2014.
M. P. Kadaba, H. K. H. Ramakrishnan, and M. E. M. Wootten, "Measurement of lower extremity kinematics during level walking," J. Orthop. Res., vol. 8, No. 3, pp. 383-392, May 1990.
M. R. Tucker, C. Shirota, O. Lambercy, J. S. Sulzer, and R. Gassert, "Design and Characterization of an Exoskeleton for Perturbing the Knee during Gait," IEEE Trans. Biomed. Eng., vol. 64, No. 10, pp. 2331-2343, Oct. 2017.
M. Riedmiller, "Neural fitted Q iteration—First experiences with a data efficient neural Reinforcement Learning method," in 16th Eur. Conf. Mach. Learn. Porto, Portugal: Springer, 2005, pp. 317-328.
M. Riedmiller, M. Montemerlo, and H. Dahlkamp, "Learning to drive a real car in 20 minutes," in Front. Converg. Biosci. Inf. Technol. Jeju, Korea: Springer, 2007, pp. 645-650.
M. Riedmiller, T. Gabel, R. Hafner, and S. Lange, "Reinforcement learning for robot soccer," Auton. Robots, vol. 27, No. 1, pp. 55-73, Jul. 2009.
N. Thatte, H. Duan, and H. Geyer., "A method for online optimization of lower limb assistive devices with high dimensional parameter spaces," in IEEE Int. Conf. Robot. Autom., 2018, pp. 5380-5385.
P. J. Werbos, "A menu of designs for reinforcement learning over time," in Neural networks Control, MIT press, 1990, ch. 3, pp. 67-95.
P. J. Werbos, "Beyond Regression: New Tools for Prediction and Analysis in the Behavioral Sciences," PhD thesis, Harvard University, 1974.
P. J. Werbos, "Building and Understanding Adaptive Systems: A Statistical/Numerical Approach to Factory Automation and Brain Research," IEEE Trans. Syst. Man Cybern., vol. 17, No. 1, pp. 7-20, Jan. 1987.
P. Malcolm, R. E. Quesada, J. M. Caputo, and S. H. Collins, "The influence of push-off timing in a robotic ankle-foot prosthesis on the energetics and mechanics of walking," J. Neuroeng. Rehabil., vol. 12, No. 21, Feb. 2015.
R. D. Gregg, T. Lenzi, L. J. Hargrove, and J. W. Sensinger, "Virtual constraint control of a powered prosthetic leg: From simulation to experiments with transfemoral amputees," IEEE Trans. Robot., vol. 30, No. 6, pp. 1455-1471, Dec. 2014.
R. Enns and J. Si, "Helicopter flight-control reconfiguration for main rotor actuator failures," J. Guid. Control. Dyn., vol. 26, No. 4, pp. 572-584, Jul. 2003.
R. Enns and J. Si, "Helicopter Trimming and Tracking Control Using Direct Neural Dynamic Programming," IEEE Trans. Neural Netw., vol. 14, No. 4, pp. 929-939, Jul. 2003.
R. Hafner and M. Riedmiller, "Neural reinforcement learning controllers for a real robot application," in Proc.—IEEE Int. Conf. Robot. Autom., Roma, Italy, Apr. 2007, pp. 2098-2103.
R. Hafner and M. Riedmiller, "Reinforcement learning in feedback control : Challenges and benchmarks from technical process control," Mach. Learn., vol. 84, No. 1, pp. 137-169, Jul. 2011.
S. Au, M. Berniker, and H. Herr, "Powered ankle-foot prosthesis to assist level-ground and stair-descent gaits," Neural Netw., vol. 21, No. 4, pp. 654-666, Apr. 2008.
S. Gu, E. Holly, T. Lillicrap, and S. Levine, "Deep reinforcement learning for robotic manipulation with asynchronous off-policy updates," in Proc.—IEEE Int. Conf. Robot. Autom, 2017.
S. K. Au, J. Weber, and H. Herr, "Powered ankle-foot prosthesis improves walking metabolic economy," IEEE Trans. Robot., vol. 25, No. 1, pp. 51-66, Feb. 2009.
S. L. Delp and A. c. Frank, "OpenSim: Open-source software to create and analyze dynamic simulations of movement," IEEE Trans. Biomed. Eng., vol. 54, No. 11, pp. 1940-1950, Nov. 2007.
S. Levine, C. Finn, T. Darrell, and P. Abbeel, "End-to-End Training of Deep Visuomotor Policies," J. Mach. Learn. Res., vol. 17, No. 1, pp. 1334-1373, Jan. 2016.
S. Levine, N. Wagener, and P. Abbeel, "Learning contact-rich manipulation skills with guided policy search," in IEEE Int. Conf. Robot. Autom., 2015, pp. 156-163.
S. Pfeifer, H. Vallery, M. Hardegger, R. Riener, and E. J. Perreault, "Model-based estimation of knee stiffness," IEEE Trans. Biomed. Eng., vol. 59, No. 9, pp. 2604-2612, Sep. 2012.
T. Gabel and M. Riedmiller, "Adaptive Reactive Job-Shop Scheduling With Reinforcement Learning Agents," Int. J. Inf. Technol. Intell. Comput., vol. 24, No. 4, 2008.
W. Guo, F. Liu, J. Si, D. He, R. Harley, and S. Mei, "Online Supplementary ADP Learning Controller Design and Application to Power System Frequency Control With Large-Scale Wind Energy Integration," IEEE Trans. Neural Networks Learn. Syst., vol. 27, No. 8, pp. 1748-1761, Mar. 2016.
W. Guo, J. Si, F. Liu, and S. Mei, "Policy Approximation in Policy Iteration Approximate Dynamic Programming for Discrete-Time Nonlinear Systems," IEEE Trans. Neural Networks Learn. Syst., vol. 29, No. 7, pp. 2794-2807, Jul. 2018.
W. Montgomery, A. Ajay, C. Finn, P. Abbeel, and S. Levine, "Reset-free guided policy search: Efficient deep reinforcement learning with stochastic initial states," in IEEE Int. Conf. Robot. Autom., 2017, pp. 3373-3380.
Wen, Yue, et al. "Online reinforcement learning control for the personalization of a robotic knee prosthesis." IEEE transactions on cybernetics 50.6 (2019): 2346-2356.
X. Gao, J. Si, Y. Wen, M. Li, and H. He, "Adaptive Batch Policy Iteration Parameter Optimization for Powered Prosthetic Knee with Human in the Loop," Submitt. to IEEE Trans. Neural Networks Learn. Syst., 2018.
Y. Ding, M. Kim, S. Kuindersma, and C. J. Walsh, "Human-in-the-loop optimization of hip assistance with a soft exosuit during walking," Sci. Robot., vol. 3, No. 15, p. eaar5438, Feb. 2018.
Y. Wang, W. X. Zheng, and H. Zhang, "Dynamic event-based control of nonlinear stochastic systems," IEEE Trans. Automat. Contr., vol. 62, No. 12, pp. 6544-6551, Dec. 2017.

(56) References Cited

OTHER PUBLICATIONS

Y. Wen, J. Si, A. Brandt, X. Gao, and H. Huang, "Online reinforcement learning control for the personalization of a robotic knee prosthesis," IEEE Trans. Cybern., Jan. 2019, doi:10.1109/TCYB.2019.2890974.

Y. Wen, J. Si, X. Gao, S. Huang, and H. Huang, "A New Powered Lower Limb Prosthesis Control Framework Based on Adaptive Dynamic Programming," IEEE Trans. Neural Networks Learn. Syst., vol. 28, No. 9, pp. 2215-2220, Sep. 2017.

Y. Wen, M. Liu, J. Si, and H. Huang, "Adaptive Control of Powered Transfemoral Prostheses Based on Adaptive Dynamic Programming," in 38th Annu. Int. Conf. IEEE Eng. Med. Biol. Soc., Orlando, FL, USA, 2016.

* cited by examiner

| Phase | Stance Flexion | | | Stance Extension | | | Swing Flexion | | | Swing Extension | | |
|---|---|---|---|---|---|---|---|---|---|---|---|---|
| Impedance Parameter[a] | $k$ | $\theta_e$ | $b$ | $k$ | $\theta_e$ | $b$ | $k$ | $\theta_e$ | $b$ | $k$ | $\theta_e$ | $b$ |
| TF S1 | 2.077 | 10.020 | 0.069 | 3.644 | 10.399 | 0.177 | 0.515 | 36.000 | 0.004 | 0.658 | 14.096 | 0.049 |
| TF S2 | 2.423 | 9.842 | 0.089 | 2.534 | 13.366 | 0.165 | 0.740 | 35.098 | 0.020 | 0.609 | 12.546 | 0.046 |
| TF S3 | 2.068 | 11.099 | 0.103 | 2.493 | 13.749 | 0.177 | 0.601 | 32.779 | 0.006 | 0.657 | 12.814 | 0.066 |
| AB S1 | 1.948 | 9.914 | 0.066 | 2.542 | 12.875 | 0.133 | 1.853 | 36.754 | 0.013 | 0.967 | 24.068 | 0.011 |
| AB S2 | 2.783 | 8.241 | 0.067 | 2.288 | 14.010 | 0.127 | 0.305 | 52.407 | 0.019 | 0.522 | 16.768 | 0.014 |
| AB S3 | 1.578 | 10.774 | 0.107 | 1.571 | 19.581 | 0.237 | 3.294 | 36.444 | 0.042 | 0.625 | 16.334 | 0.057 |

FIG. 11

TABLE I

BOUNDS ON THE ACTIONS

| Gait Phase | $K$ ($N$-$m$/$deg$) | $\theta_e$ ($deg$) | $B$ ($N$-$m$-$s$/$deg$) |
|---|---|---|---|
| STF | [−0.1, 0.1] | [−1, 1] | [−0.001, 0.001] |
| STE | [−0.1, 0.1] | [−1, 1] | [−0.001, 0.001] |
| SWF | [−0.01, 0.01] | [−2, 2] | [−0.001, 0.001] |
| SWE | [−0.01, 0.01] | [−1, 1] | [−0.001, 0.001] |

Algorithm 1 Offline Approximate Policy Iteration

Input: training dataset $D = \{(x_n, u_n, x'_n), n = 1, 2, \ldots, N\}$

Output: optimal cost function $Q^*(x, u)$ and policy $\pi^*(x_k)$

1: for $i = 1, 2, \ldots, i_{max}$ do

2: Get $S^{(i)}$ from (15) and $\hat{Q}^{(i)}(x, u)$ from (13)

3: Get policy $\pi^{(i+1)}(x)$ from (17)

4: end for

5: return $Q^*(x, u) = \hat{Q}^{(i)}(x, u)$ and $\pi^*(x) = \pi^{(i+1)}(x)$

FIG. 13

SYSTEMS AND METHODS FOR REINFORCEMENT LEARNING CONTROL OF A POWERED PROSTHESIS

CROSS-REFERENCE TO RELATED APPLICATIONS

This application is a national stage application filed under 35 U.S.C. § 371 of PCT/US2020/060703 filed Nov. 16, 2020, which claims the benefit of U.S. provisional patent application No. 62/961,289, filed on Jan. 15, 2020, and entitled "SYSTEMS AND METHODS FOR REINFORCEMENT LEARNING CONTROL OF A POWERED PROSTHESIS," the disclosures of which are expressly incorporated herein by reference in-their entireties.

STATEMENT REGARDING FEDERALLY FUNDED RESEARCH

This invention was made with government support under grant numbers 1563454, 1563921, and 1808752 awarded by the National Science Foundation. The government has certain rights in the invention.

BACKGROUND

Advances in robotic prostheses, compared to conventional passive devices, have shown great promise to further improve the mobility of individuals with lower limb amputation. Robotic prosthesis control typically consists of a finite-state machine and a low-level controller to regulate the prosthetic joint impedance. Existing robotic prosthesis controllers rely on a large number of configurable parameters (e.g., 12-15 for knee prostheses and 9-15 for ankle-foot prostheses) for a single locomotion mode such as level ground walking. The number of parameters grows when the number of included locomotion modes increases. These control parameters need to be personalized to individual user differences such as height, weight, and physical ability. Currently in clinics, prosthesis control parameters are personalized manually, which can be time, labor, and cost intensive.

Researchers have attempted to improve the efficiency of prosthesis tuning through three major approaches. The first approach is to estimate the control impedance parameters with either a musculoskeletal model or measurements of biological joint impedance. However, these methods have not been validated for real prosthesis control. The second solution does not directly address parameter tuning but aims at reducing the number of control parameters. The third method, which is described in U.S. Pat. No. 10,335,294, issued Jul. 2, 2019, provides automatic parameter tuning by coding prosthetists' decisions.

There is therefore a need in the art for new approaches to solve this prosthesis parameter tuning problem.

SUMMARY

An example system for tuning a powered prosthesis is described herein. The system can include a powered prosthesis including a joint, a motor mechanically coupled to the joint, a plurality of sensors, a finite state machine, and an impedance controller. The motor is configured to drive the joint. Additionally, the sensors are configured to measure a plurality of gait parameters associated with a subject, and the finite state machine is configured to determine a gait cycle state based on the measured gait parameters. The impedance controller is configured to output a control signal for adjusting a torque of the motor, where the torque is adjusted as a function of the measured gait parameters and a plurality of impedance control parameters, and where the impedance control parameters are dependent on the gait cycle state. The system can also include a reinforcement learning controller operably connected to the powered prosthesis. The reinforcement learning controller is configured to tune at least one of the impedance control parameters to achieve a target gait characteristic using a training data set.

In some implementations, the system is configured for online reinforcement learning control. In these implementations, the training data set includes real-time data collected by the sensors while the subject is walking. Optionally, the reinforcement learning controller is configured to tune the at least one of the impedance control parameters to achieve the target gait characteristic in about 300 gait cycles. Alternatively or additionally, the reinforcement learning controller is optionally configured to tune the at least one of the impedance control parameters to achieve the target gait characteristic in about 10 minutes.

Alternatively or additionally, the reinforcement learning controller is further configured to receive the measured gait parameters, and derive a state of the powered prosthesis based on the measured gait parameters. The at least one of the impedance control parameters is tuned to achieve the target gait characteristic in response to the state of the powered prosthesis.

Alternatively or additionally, the reinforcement learning controller includes a plurality of direct heuristic dynamic programming (dHDP) blocks, each dHDP block being associated with a different gait cycle state. Each dHDP block can include at least one neural network. For example, in some implementations, each dHDP block includes an action neural network (ANN) and a critic neural network (CNN).

In some implementations, the system is configured for offline reinforcement learning control. In these implementations, the training data set includes offline training data. Optionally, the reinforcement learning controller is configured to execute an approximate policy iteration. Alternatively or additionally, the training data set can optionally further include real-time data collected by the sensors while the subject is walking. For example, the reinforcement learning controller is further configured to receive the measured gait parameters, derive a state of the powered prosthesis based on the measured gait parameters, and refine the at least one of the impedance control parameters to achieve the target gait characteristic in response to the state of the powered prosthesis.

Alternatively or additionally, the impedance control parameters include a respective set of impedance control parameters for each of a plurality of gait cycle states.

Alternatively or additionally, the gait cycle state is one of a plurality of level ground walking gait cycle states. For example, the level ground walking gait cycle states include stance flexion (STF), stance extension (STE), swing flexion (SWF), and swing extension (SWE).

Alternatively or additionally, the impedance control parameters include at least one of a stiffness, an equilibrium position, or a damping coefficient.

Alternatively or additionally, the target gait characteristic is a gait characteristic of a non-disabled subject.

Alternatively or additionally, the measured gait parameters include at least one of a joint angle, a joint angular velocity, a duration of a gait cycle state, or a load applied to the joint.

Alternatively or additionally, the joint is a prosthetic knee joint, a prosthetic ankle joint, or a prosthetic hip joint.

An example method for tuning a powered prosthesis is also described herein. The powered prosthesis can include a joint, a motor mechanically coupled to the joint, a plurality of sensors, a finite state machine, and an impedance controller. The method can include receiving a plurality of gait parameters associated with a subject from at least one of the sensors, and determining, using the finite state machine, a gait cycle state based on the received gait parameters. The method can also include training a reinforcement learning controller with a training data set to tune at least one of a plurality of impedance control parameters to achieve a target gait characteristic. The method can further include outputting, using the impedance controller, a control signal for adjusting a torque of the motor, where the torque is adjusted as a function of the measured gait parameters and the impedance control parameters, and where the impedance control parameters are dependent on the gait cycle state.

In some implementations, the method is for online reinforcement learning control. In these implementations, the training data set includes real-time data collected by the sensors while the subject is walking. For example, the method can further include deriving a state of the powered prosthesis based on the received gait parameters. The step of training the reinforcement learning controller can include tuning the at least one of the impedance control parameters to achieve the target gait characteristic in response to the state of the powered prosthesis.

In some implementations, the method is for offline reinforcement learning control. In these implementations, the training data set includes offline training data. For example, the method can further include collecting the offline training data. The step of training the reinforcement learning controller can include tuning the at least one of the impedance control parameters to achieve the target gait characteristic based on the offline training data. Optionally, the training data set can further include real-time data received from the sensors while the subject is walking. The method can further include deriving a state of the powered prosthesis based on the received gait parameters. The step of training the reinforcement learning controller further includes refining the at least one of the impedance control parameters to achieve the target gait characteristic in response to the state of the powered prosthesis.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 3A illustrates the offline training process (Algorithm 1). Here $x_n$ and $u_n$ are state and action of the nth offline collected sample, respectively. The optimal policy $\pi^*$ is obtained after training. FIG. 3B illustrates the online testing process. State $x_k$ is computed based on real-time measurements, then action $u_k$, i.e., the adjustment to the impedance parameters, is computed according to the offline trained policy $\pi^*(x_k)$. Finally, according to the well established FSM framework, a knee joint torque T is created based on the impedance control law (2). FIG. 3C illustrates target points and control points are defined on gait trajectories. The dashed line shows knee kinematics of normal human walking and the solid line represents actual measured knee kinematics. The crosses are target points in the normal knee kinematics and black crosses are control points of measured knee kinematics. State $x_k$ is formulated using the vertical and horizontal distances between the control points and the target points.

FIG. 9A illustrates stance flexion phase, FIG. 9B illustrates stance extension phase, FIG. 9C illustrates swing flexion phase, and FIG. 9D illustrates swing extension phase. The red dots were times when the −1 reinforcement signals incurred, and the blue dots were times when the −0.8 reinforcement signals incurred. The horizontal blue areas, which centered at zero, indicate the tolerance ranges for each feature. The paired horizontal red lines indicate the allowed maximum and minimum exploration limits for each feature.

FIG. 10A illustrates stance flexion phase, FIG. 10B illustrates stance extension phase, FIG. 10C illustrates swing flexion phase, and FIG. 10D illustrates swing extension phase. The meanings of the red and blues dots are the same.

FIG. 11 is a table with post-tuning impedance parameters of three testing sessions for two subjects. k (Nm/deg) is the stiffness coefficient; $\vartheta_e$ (deg) is the equilibrium position; b (Nms/deg) is the damping coefficient.

FIG. 12A illustrates trends of angle error along tuning iterations. FIG. 12B illustrates trends of duration error along tuning iterations. FIG. 12C illustrates changing J values as learning proceeded. FIG. 12D illustrates RMSE along tuning iterations FIG. 13 is a table illustrating the upper and lower bounds for acceptable actions and an algorithm for offline approximate policy iteration.

FIG. 14A illustrates stance flexion. FIG. 14B illustrates stance extension. FIG. 14C illustrates swing flexion. FIG. 14D illustrates swing extension.

FIG. 15A illustrates the first set of initial parameters. FIG. 15B illustrates the second set of initial parameters. FIG. 15C illustrates the third set of initial parameters.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. While implementations will be described for a automatically tuning impedance control parameters of a powered knee prosthesis, it will become evident to those skilled in the art that the implementations are not limited thereto, but are applicable for automatically tuning impedance control parameters of other powered prostheses.

As used herein, the terms "about" or "approximately", when used in reference to a time or number of gait cycles need to tune impedance control parameters, mean within plus or minus 10% percentage of the referenced time or number of gait cycles.

Figure 1A:
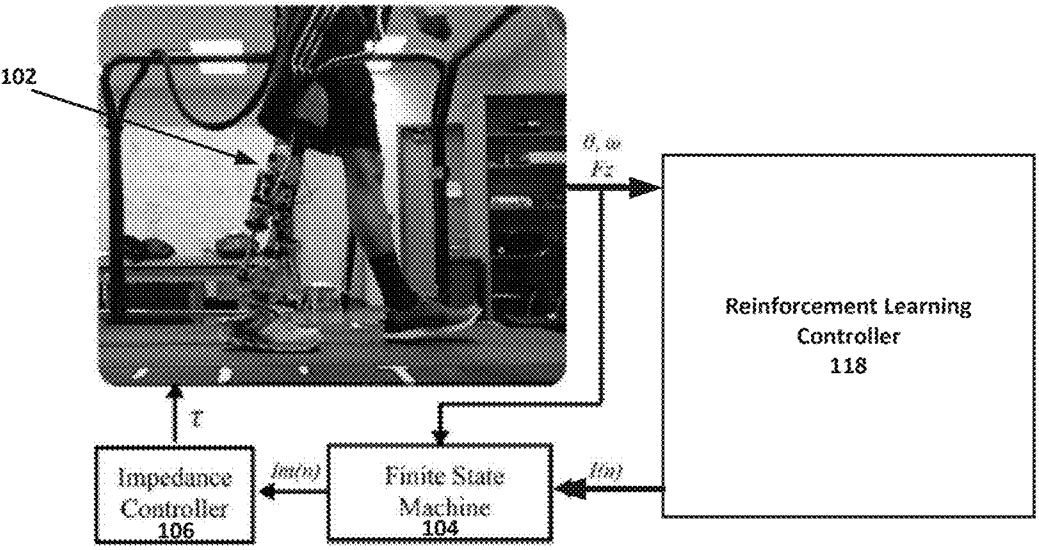
FIG. 1A is a block diagram of a system for tuning a powered prothesis according to implementations described herein.

With reference to FIG. 1A, a block diagram of an example system for tuning a powered prosthesis is shown. Optionally, the powered prosthesis can be a powered knee prosthesis (PKP). Although examples are provided where the powered prosthesis is a PKP herein, it should be understood that that the techniques described herein can be used for tuning impedance control parameters for other powered prosthesis devices. For example, the techniques described herein can be used for tuning impedance control parameters for a prosthetic leg, which can include one or more prosthetic joints (e.g., prosthetic hip, knee, and/or ankle joints). Additionally, a prosthetic leg can include combinations of prosthetic joints. Additionally, a bilateral amputee uses two prosthetic legs, where each prosthetic leg can include one or more prosthetic joints. This disclosure contemplates that the techniques described herein can be used for tuning the impedance control parameters for one or more of the prosthetic joints in a prosthetic leg. In addition, this disclosure contemplates that the techniques described herein can be used for tuning the impedance control parameters for passive prosthetic leg, exoskeletons and/or limb rehabilitation robots.

The system can include a powered prosthesis 102 including a joint, a motor mechanically coupled to the joint, a plurality of sensors, a finite state machine 104, and an impedance controller 106. This disclosure contemplates that the powered prosthesis 102, finite state machine 104, and impedance controller 106 can be operably connected by any suitable communication link. For example, a communication link may be implemented by any medium that facilitates data exchange including, but not limited to, wired, wireless and optical links.

Figure 1B:
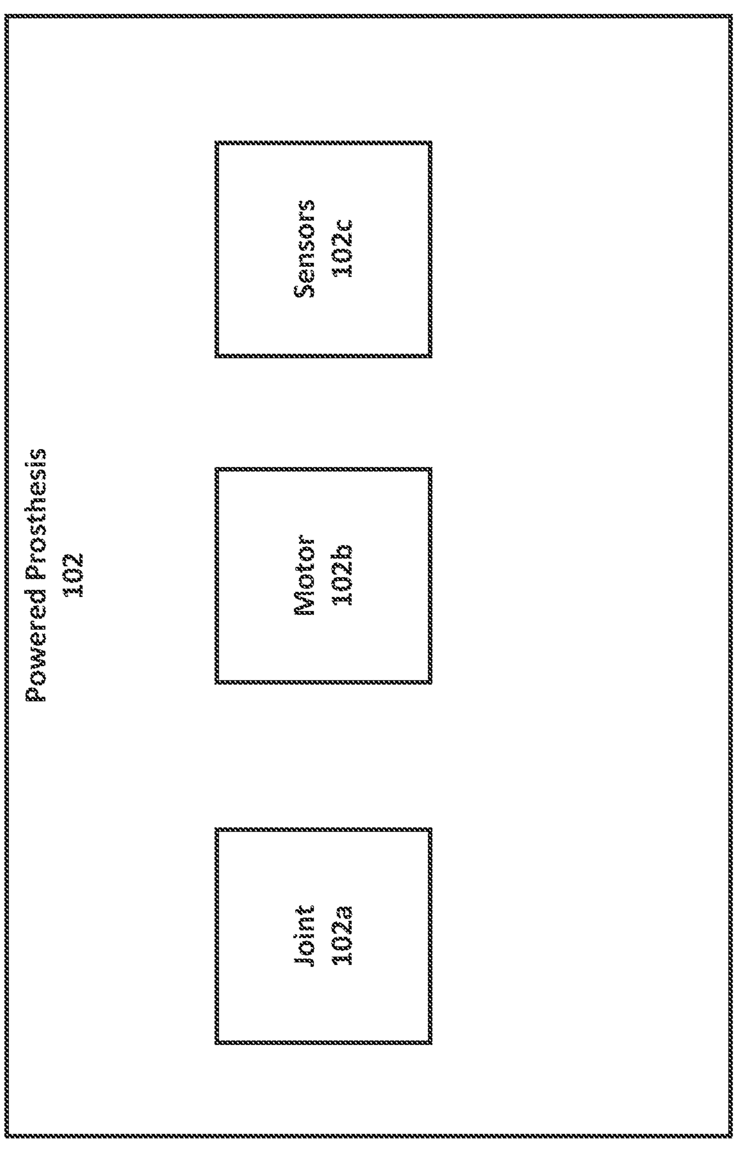
FIG. 1B is a block diagram of an example powered prothesis according to implementations described herein.

Referring now to FIG. 1B, a block diagram of the powered prosthesis 102 is shown. For example, the powered prosthesis 102 includes the joint 102*a*, the motor 102*b*, and the sensors 102*c*. The motor 102*b* is configured to drive the joint 102*a*. For example, an example PKP can include a prosthetic knee joint having a moment arm and pylon that is driven by a direct current motor through a ball screw. Additionally, the sensors 102*c* are configured to measure a plurality of gait parameters associated with a subject. The gait parameters can optionally include a joint angle, a joint angular velocity, a duration of a gait cycle state, and/or a load applied to the joint. For example, the sensors 102*c* can include a sensor for measuring joint angle (e.g., a potentiometer), a sensor for measuring joint angular velocity (e.g., an encoder operably connected to the motor), and a sensor for measuring ground reaction force (GRF) (e.g., a load sensor such as a 6 degree of freedom load cell). The sensors 102*c* can optionally be embedded in the powered prosthesis. In addition, the gait parameters can be sampled using a multi-functional data acquisition card. The gait parameters can then be communicated to the finite state machine 104, the impedance controller 106, and/or the reinforcement learning controller 108 as described herein. It should be understood that the gait parameters and sensors described above are provided only as examples. This disclosure contemplates that other gait parameters can be measured including, but not limited to, angular acceleration, angular jerk, foot orientation, shank orientation, thigh orientation, trunk orientation (trunk motion arc), lower limb segment orientation, hip height, knee height, ankle height, location of foot center of pressure, speed of foot center of pressure, acceleration of foot center of pressure, location of center of mass, velocity of center of mass, and/or acceleration of center of mass. In addition, these gait parameters can be measured using one or more of the following sensors: a foot switch, an accelerometer, an inertial moment unit, a foot pressure sensor, a strain gauge, force plate, and/or a motion capture system (e.g., an imaging system).

Referring again to FIG. 1A, the finite state machine 104 is configured to determine a gait cycle state based on the measured gait parameters. The measured gait parameters can include one or more of a joint angle or position (θ), a joint angular velocity (ω), and ground reaction force ($F_z$). Ground reaction force is also sometimes referred to herein as "GRF". It should be understood that the measured gait parameters listed above are only provided as examples. This disclosure contemplates that the measured gait parameters can optionally include other parameters including, but not limited to, a duration of a gait cycle state and/or a load applied to the joint. The measured gait parameters are provided to and received by the finite state machine 104, the impedance controller 106, and the reinforcement learning controller 108. Gait cycle states can be defined based on the expected values of the gait parameters (such as joint angle, joint angular velocity, and ground reaction force) in the respective gait cycle states. The gait cycle states of the powered prosthesis 102 can be the same gait cycle states defined by clinicians to describe gait cycle for abled-body subjects during level ground walking, for example. The level ground walking gait cycle can be divided into a plurality of gait cycle states (or phases)—stance flexion (STF), stance extension (STE), swing flexion (SWF), and swing extension (SWE). It should be understood that gait cycles are not limited to level ground walking and can include, but are not limited to, other walking cycles such as ramp ascent/descent and stair ascent/descent. The finite state machine 104 can be configured to detect transitions between the gait cycle states by monitoring the measured gait parameters and comparing the measured gait parameters to the gait cycle state definitions. Alternatively or additionally, the powered prosthesis 102 can optionally include a computing device configured to detect one or more gait events including, but not limited to, heel strike, toe off, and/or foot flat. For example, a gait event can be defined based on the expected values of the gait parameters such as joint angle, joint angular velocity, ground reaction force, and foot pressure distribution during the gait event. Thus, the computing device can be configured to detect a gait event by monitoring the measured gait parameters and comparing the measured gait parameters to the gait event definition. Optionally, in some implementations, the finite state machine 104 can use information regarding gait events to determine the gait cycle state.

The impedance controller 106 is configured to output a control signal for adjusting a torque of the motor. The impedance controller 106 can be operably connected to the motor of the powered prosthesis 102 using any suitable communication link that facilitates data exchange. For example, the impedance controller 106 can adjust the torque as a function of the measured gait parameters and a plurality of impedance control parameters as shown by:

$$\tau_m = k_m(\theta - \theta e_m) + b_m\omega$$

where $\tau_m$ is torque, joint angle (θ) and angular velocity (ω) are the measured gait parameters (e.g., measured using the sensors described above) and stiffness ($k_m$), equilibrium position ($\theta e_m$), and damping coefficient ($b_m$) are the impedance control parameters.

The impedance control parameters are dependent on gait cycle state. For example, each of stiffness ($k_m$), equilibrium position ($\theta e_m$), and damping coefficient ($b_m$) can have a respective value for each of gait cycle states STF, STE, SWF, and SWE. In other words, the impedance control parameters can include a respective set of impedance control parameters for each of a plurality of gait cycle states. Thus, with four level ground walking gait cycle states, there would be twelve (12) total impedance parameters to be configured for each locomotion mode. The measured gait parameters (joint angle (θ) and angular velocity (ω)) are received by the impedance controller 106, which then adjust the torque ($\tau_m$) as a function of the measured gait parameters and the impedance control parameters (stiffness ($k_m$), equilibrium position ($\theta e_m$), and damping coefficient ($b_m$)) by outputting a control signal for controlling the motor of the powered prosthesis 102. It should be understood that stiffness ($k_m$), equilibrium position ($\theta e_m$), and damping coefficient ($b_m$) are provided only as example impedance control parameters. This disclosure contemplates using any impedance control parameters in the techniques described herein including, but not limited to, linear or nonlinear stiffness, equilibrium position, and/or linear or nonlinear damping coefficients.

The system can also include a reinforcement learning controller 108 operably connected to the powered prosthesis 102. The powered prosthesis 102 and the reinforcement learning controller 108 can be operably connected by any suitable communication link. For example, a communication link may be implemented by any medium that facilitates data exchange including, but not limited to, wired, wireless and optical links. The reinforcement learning controller 108 is configured to tune at least one of the impedance control parameters to achieve a target gait characteristic using a training data set. Optionally, the target gait characteristic is a gait characteristic of a non-disabled subject.

Figure 2:
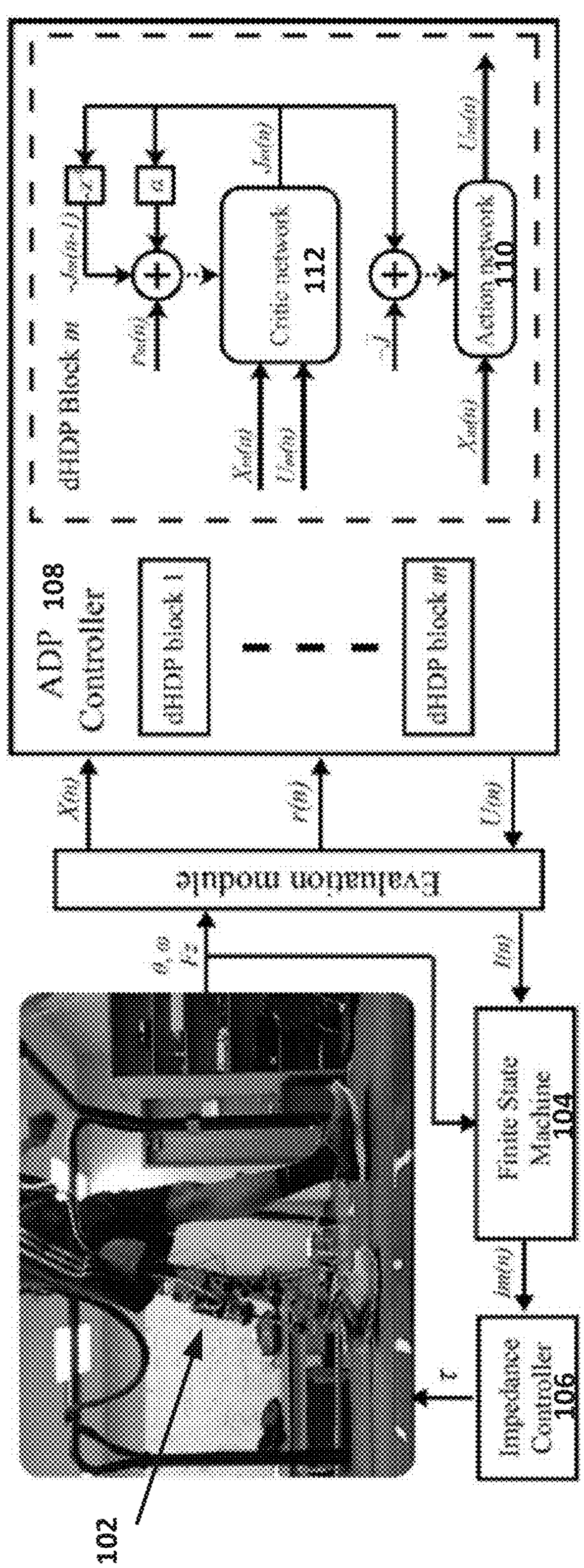
FIG. 2 is a block diagram of an ADP-tuner, an automatic robotic knee control parameter tuning scheme by dHDP with amputee in the loop. The learning control system operates at three different time scales: 1) real-time impedance controller provides outputs at 100 Hz to regulate the joint torque; 2) the finite-state machine runs at the gait frequency (denoted by time index g) with four phases per gait cycle; 3) the dHDP generated control is updated $l_{m,n}$ every few gaits (denoted by time index n) to update the impedance parameters. The respective variables in the figure are defined and discussed below. The ADP-tuner consists of four dHDP blocks (m=1, 2, 3, 4) corresponding to four gait phases in the finite-state machine impedance controller.

Referring now to FIG. 2, in some implementations, the system is configured for online reinforcement learning control. In these implementations, the training data set includes real-time data collected by the sensors while the subject is walking. The system of FIG. 2 includes the prosthetic prosthesis 102, the finite state machine 104, the impedance controller 106, and the reinforcement learning controller 108. The reinforcement learning controller 108 is further configured to receive the measured gait parameters, and derive a state of the powered prosthesis 102 based on the measured gait parameters (see e.g., Eqn. (5) below). Thus, in this implementation, the reinforcement learning controller 108 is configured to tune the impedance control parameter(s) while the subject is walking (i.e., in real-time on the fly). As described above, the at least one of the impedance control parameters is tuned to achieve the target gait characteristic in response to the state of the powered prosthesis 102.

As shown in FIG. 2, the reinforcement learning controller 108 includes a plurality of direct heuristic dynamic programming (dHDP) blocks (e.g., dHDP block 1 . . . dHDP block m), each dHDP block being associated with a different gait cycle state. For example, there is a respective dHDP block for each gait cycle (e.g., different dHDP blocks for STF, STE, SWF, SWE, etc. gait cycle states). It should be understood that the number of dHDP blocks depends on the number of gait cycle states. Additionally, each dHDP block can include at least one neural network. For example, in some implementations, each dHDP block includes an action neural network (ANN) or action network 110 and a critic neural network (CNN) or critic network 112. Example ANN or action network 110 and CNN or critic network 112 are described in Example 1 below.

A neural network is a computing system including a plurality of interconnected neurons (e.g., also referred to as "nodes"). This disclosure contemplates that the nodes can be implemented using a computing device (e.g., a processing unit and memory as described herein). The nodes can optionally be arranged in a plurality of layers such as input layer, output layer, and one or more hidden layers. Each node is connected to one or more other nodes in the neural network. For example, each layer is made of a plurality of nodes, where each node is connected to all nodes in the previous layer. The nodes in a given layer are not interconnected with one another, i.e., the nodes in a given layer function independently of one another. As used herein, nodes in the input layer receive data from outside of the neural network (e.g., the states described herein), nodes in the hidden layer(s) modify the data between the input and output layers, and nodes in the output layer provide the results (e.g., the actions described herein). Each node is configured to receive an input, implement an activation function (e.g., binary step, linear, sigmoid, tan H, or rectified linear unit (ReLU) function), and provide an output in accordance with the activation function. Additionally, each node is associated with a respective weight. Neural networks are trained with a data set (e.g., the online training data described herein) to minimize the cost function, which is a measure of the neural network's performance. Training algorithms include, but are not limited to, backpropagation. The training algorithm tunes the node weights and/or bias to minimize the cost function. It should be understood that any algorithm that finds the minimum of the cost function can be used to for training the neural network. It should be understood that the ANNs and CNNs described herein are types of neural networks.

The states input into the reinforcement learning controller 108 are the measured gait parameters (e.g., gait parameters including, but not limited to, joint angle, angular velocity, GRF, duration of gait cycle state, load), and the actions output by the reinforcement learning controller 108 are the tuned impedance control parameters (e.g., impedance control parameters including, but not limited to, stiffness, equilibrium position, damping coefficient). Additionally, as described above, there is a respective dHDP block for each gait cycle (e.g., different dHDP blocks for STF, STE, SWF, SWE, etc. gait cycle states). It should be understood that the number of dHDP blocks depends on the number of gait cycle states. Additionally, it should be understood that the number and/or types of states and actions described herein are provided only as examples.

As noted above, the reinforcement learning controller 108 is configured to tune the impedance control parameter(s) in real-time while the subject is walking. Optionally, the reinforcement learning controller 108 is configured to tune the at least one of the impedance control parameters to achieve the target gait characteristic in about 300 gait cycles. It should be understood that 300 gait cycles is provided only as an example. This disclosure contemplates that the impedance control parameter(s) can be tuned to achieve the target gait characteristic from between about 240 gait cycles and about 360 gait cycles. Alternatively or additionally, the reinforcement learning controller 108 is optionally configured to tune the at least one of the impedance control parameters to achieve the target gait characteristic in about 10 minutes. It should be understood that 10 minutes is provided only as an example. This disclosure contemplates that the impedance control parameter(s) can be tuned to achieve the target gait characteristic from between about 8 minutes and about 12 minutes.

Figures 3A, 3B, 3C:
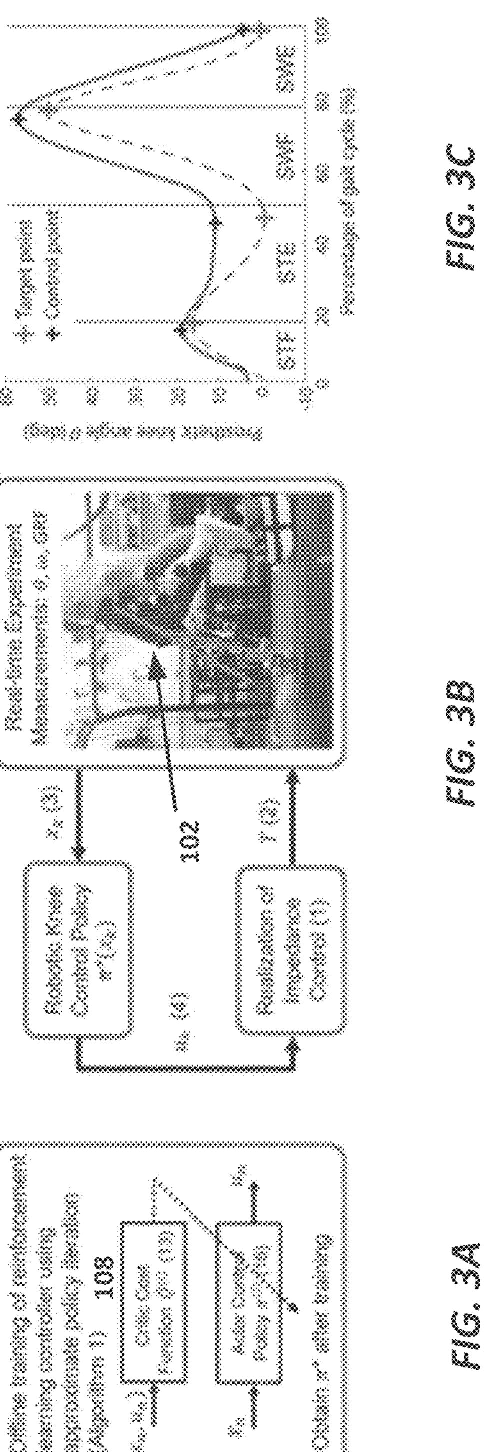
FIGS. 3A-3C illustrate an overview of offline reinforcement learning controller design and online human subject testing.

Referring now to FIGS. 3A-3C, in some implementations, the system is configured for offline reinforcement learning control. In these implementations, the training data set includes offline training data. The system of FIGS. 3A-3C includes the prosthetic prosthesis 102 and the reinforcement learning controller 108. Although not shown in FIGS. 3A-3C, the system also includes a finite state machine (e.g., the finite state machine 104 of FIG. 1A) and an impedance controller (e.g., the impedance controller 106 of FIG. 1A). The reinforcement learning controller 108 is configured to execute an approximate policy iteration. An example approximate policy iteration algorithm is described in Example 2 below. In this implementation, the reinforcement learning controller 108 is configured to tune the impedance control parameter(s) with previously collected data (i.e., tuning is not in real-time while the subject is walking). The states input into the reinforcement learning controller 108 are the measured gait parameters (e.g., gait parameters including, but not limited to, joint angle, angular velocity, GRF, duration of gait cycle state, load), and the actions output by the reinforcement learning controller 108 are the tuned impedance control parameters (e.g., impedance control parameters including, but not limited to, stiffness, equilibrium position, damping coefficient). It should be understood that the number and/or types of states and actions described herein are provided only as examples.

Alternatively or additionally, the training data set can optionally further include real-time data collected by the sensors while the subject is walking. For example, the reinforcement learning controller 108 can be further configured to receive the measured gait parameters, derive a state of the powered prosthesis 102 based on the measured gait parameters, and refine the at least one of the impedance control parameters to achieve the target gait characteristic in response to the state of the powered prosthesis 102. In other words, the reinforcement learning controller 108 can first be trained using offline training data and thereafter applied to control the powered prosthesis 102 in real-time and also refine the impedance control parameter(s) in real-time.

It should be appreciated that the logical operations described herein with respect to the various figures may be implemented (1) as a sequence of computer implemented acts or program modules (i.e., software) running on a computing device (e.g., the computing device described in FIG. 4), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 4:
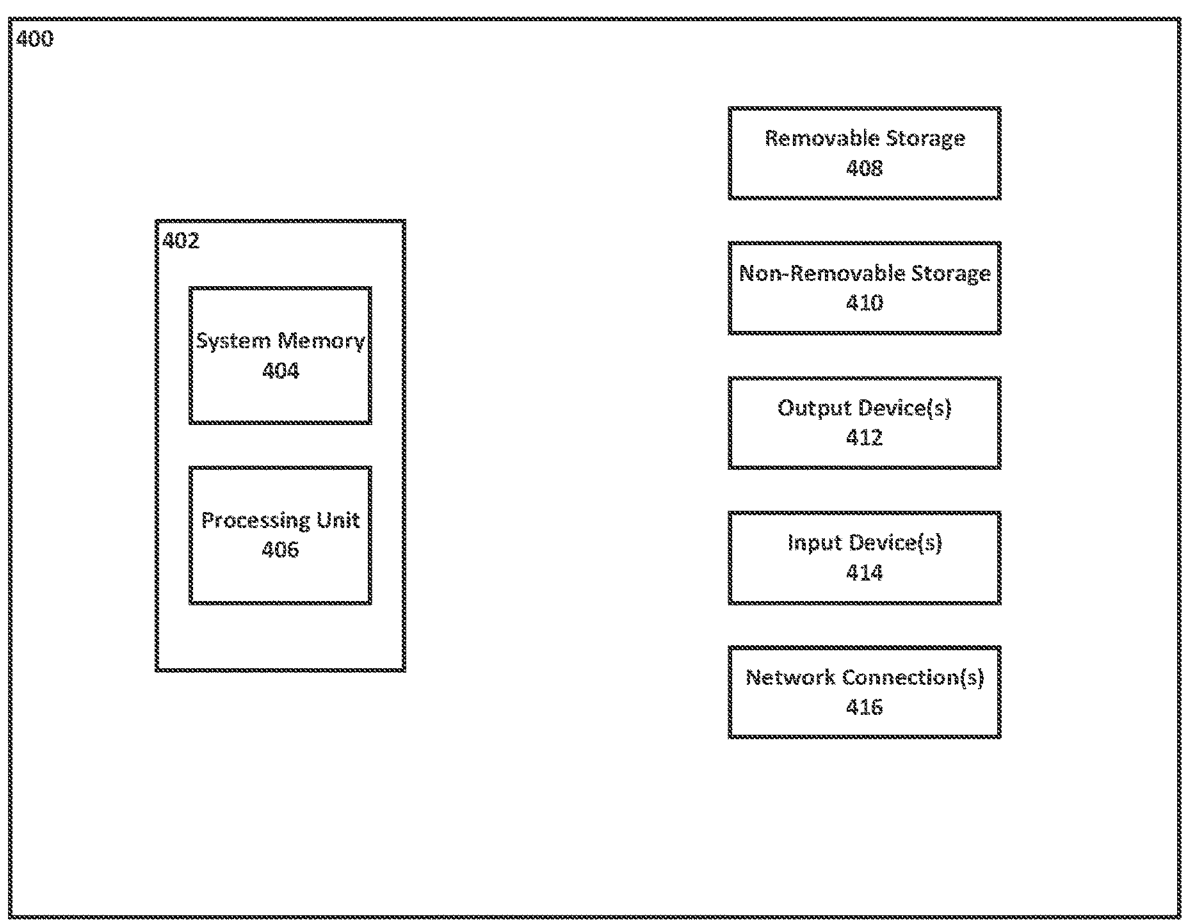
FIG. 4 is a block diagram of an example computing device.

Referring to FIG. 4, an example computing device 400 upon which the methods described herein may be implemented is illustrated. It should be understood that the example computing device 400 is only one example of a suitable computing environment upon which the methods described herein may be implemented. Optionally, the computing device 400 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 400 typically includes at least one processing unit 406 and system memory 404. Depending on the exact configuration and type of computing device, system memory 404 may be volatile (such as random access memory (RAM)), non-volatile (such as read-only memory (ROM), flash memory, etc.), or some combination of the two. This most basic configuration is illustrated in FIG. 4 by dashed line 402. The processing unit 406 may be a standard programmable processor that performs arithmetic and logic operations necessary for operation of the computing device 400. The computing device 400 may also include a bus or other communication mechanism for communicating information among various components of the computing device 400.

Computing device 400 may have additional features/functionality. For example, computing device 400 may include additional storage such as removable storage 408 and non-removable storage 410 including, but not limited to, magnetic or optical disks or tapes. Computing device 400 may also contain network connection(s) 416 that allow the device to communicate with other devices. Computing device 400 may also have input device(s) 414 such as a keyboard, mouse, touch screen, etc. Output device(s) 412 such as a display, speakers, printer, etc. may also be included. The additional devices may be connected to the bus in order to facilitate communication of data among the components of the computing device 400. All these devices are well known in the art and need not be discussed at length here.

The processing unit 406 may be configured to execute program code encoded in tangible, computer-readable media. Tangible, computer-readable media refers to any media that is capable of providing data that causes the computing device 400 (i.e., a machine) to operate in a particular fashion. Various computer-readable media may be utilized to provide instructions to the processing unit 406 for execution. Example tangible, computer-readable media may include, but is not limited to, volatile media, non-volatile media, removable media and non-removable media implemented in any method or technology for storage of information such as computer readable instructions, data structures, program modules or other data. System memory 404, removable storage 408, and non-removable storage 410 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 406 may execute program code stored in the system memory 404. For example, the bus may carry data to the system memory 404, from which the processing unit 406 receives and executes instructions. The data received by the system memory 404 may optionally be stored on the removable storage 408 or the non-removable storage 410 before or after execution by the processing unit 406.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

EXAMPLES

Example 1: Online Reinforcement Learning Control

Robotic prostheses deliver greater function than passive prostheses, but medical professionals face the challenge of tuning a large number of control parameters in order to personalize the device for individual amputee users. This problem is not easily solved by traditional control designs or the latest robotic technology. Reinforcement learning (RL) is naturally appealing. Its recent, unprecedented successes associated with AlphaZero demonstrated RL as feasible, large-scale problem solver. However, the prosthesis-tuning problem is associated with several unaddressed issues such as that it does not have a known and stable model. The continuous states and controls of the problem may result in a curse of dimensionality, and the human-prosthesis system is constantly subject to measurement noise, environment change, and human body caused variations. In this example, the feasibility of direct Heuristic Dynamic Programming (dHDP), an approximate dynamic programming (ADP) approach, to automatically tune the 12 robotic knee prosthesis parameters to meet individual human users' needs is demonstrated. The ADP-tuner was tested on two subjects (i.e. one able-bodied subject and one amputee subject) walking at a fixed speed on a treadmill. The ADP-tuner learned to reach target gait kinematics in an average of 300 gait cycles or 10 minutes of walking. Improved ADP tuning performance were observed when a previously-learned ADP controller was transferred to a new learning session with the same subject.

As described above, there is a need in the art for new approaches to solve prosthesis parameter tuning problem. Personalizing wearable robots, e.g. robotic prostheses and exoskeletons, requires optimal adaptive control solutions. Koller et al. used gradient descent method to optimize an onset time of an ankle exoskeleton to enhance able-bodied persons' gait efficiency. Zhang et al. used evolution strategy to optimize four control parameters for an ankle exoskeleton. Ding et al. applied Bayesian optimization to identify two control parameters of hip extension assistance. These methods are promising, but they have not been used for personalizing robotic prostheses potentially because it is difficult to scale up to a high dimensional (≥5) parameter space, adapt to changing conditions (e.g. weight change), or monitor the chosen performance measure in daily life (e.g. metabolic cost).

Reinforcement learning (RL) lends itself as an alternative approach to personalizing lower limb prostheses. Although it has defeated two thousand years of human GO knowledge by learning to play the game in hours. RL has not yet been applied in clinical situations with greater complexity and human interactions. For example, the control of wearable robotics introduces the additional challenge of the curse of high dimensionality in continuous state and control/action spaces, and the demand of meeting optimal performance objectives under system uncertainty, measurement noise, and unexpected disturbance. Approximate dynamic programming (ADP) is synonymous to reinforcement learning, especially in controls and operations research communities, and it has shown great promise to address the aforementioned challenges.

Adaptive critic designs are a series of ADP designs that were originally proposed by Werbos. In the last decade, the adaptive critic design has been developed and applied extensively to robust control, optimal control, and event-driven applications. The action-dependent heuristic dynamic programming (ADHDP) is similar to Q-learning but with promising scalability. New developments within the realm of ADHDP (e.g. neural fitted Q (NFQ), neural fitted Q with continuous actions (NFQCA), direct heuristic dynamic programming (direct HDP or dHDP), the forward model for learning control, fuzzy adaptive dynamic programming) have emerged and demonstrated their feasibility for complex and realistic learning control problems. Furthermore, dHDP and NFQCA (noted as a batch variant of the dHDP) algorithms are associated with perhaps most of the demonstrated applications of RL control for continuous state and control problems. The focus of this study is therefore to implement the dHDP in real time for online learning control to adaptively tune the impedance parameters of the prosthetic knee.

Prior to real experimentation involving human subjects, a simulation study was performed. An ADP-tuner for a prosthetic knee joint was designed and this control was validated on an established computational model, OpenSim, for dynamic simulations of amputee gait. dHDP was compared with NFQCA. Simulation results showed that dHDP controller enabled the simulated amputee model to learn to walk within fewer gait cycles and with a higher success rate than NFQCA. Although exciting and promising, it is unknown how dHDP performs with a real human in the loop. This is because the OpenSim model ignores human responses to actions of the prosthesis, natural gait variability, and most importantly, safety.

This is the first study to realize an ADP learning controller for a real-life situation such as the personalization of robotic prostheses for human subjects. The model-free dHDP was tailored to be data and time efficient for this application and was implemented to automatically tune 12 impedance parameters through interactions with the human-prosthesis system online. The study demonstrated, for the first time, that the proposed RL-based control is feasible and, with further development, can be made safe and practical for clinical use.

Prosthetic Knee Control Problem Formulation

FIG. 2 shows the proposed automatic tuning approach of prosthetic knee control parameters with a human in the loop. In this section, the human-prosthesis system, namely an amputee wearing a robotic knee prosthesis, is introduced.

Human Prosthesis Configuration

Both the mechanical interface and control parameters of the robotic knee prosthesis need to be personalized to each user. Humans differ in their physical conditions, such as height, weight, and muscle strength. First, the length of the pylon, alignment of the prosthesis, and the fit of the socket that interfaces the user and the prosthesis must be customized by a certified prosthetist. Then, the robotic knee control parameters must be tuned to provide personalized assistance from the knee prosthesis. The proposed automatic tuning realized as an RL-based supplementary control is shown in FIG. 2.

Prosthetic Knee Finite Machine Impedance Controller

Finite-state machine impedance control (FSM-IC, FIG. 2) is an established framework for robotic knee prosthesis control. Based on the foot-ground contact and knee joint movement, a single gait cycle is divided into four phases (corresponding to m=1, . . . , 4 in FIG. 2): the stance flexion phase (STF, m=1), stance extension phase (STE, m=2), swing flexion phase (SWF, m=3), and swing extension phase (SWE, m=4). The phase transitions can be triggered by measurements from a load cell and an angle sensor in the prosthetic device. Then, the corresponding impedance parameters $l_m$ as described in (1) are provided to impedance controller.

$$I_m = [k_m, \theta e_m, b_m]^T \tag{1}$$

Within each phase m, the robotic knee is regulated by a different impedance controller (2) to produce phase-specific dynamic properties. The impedance controller monitors the knee joint position $\vartheta$ and velocity $\omega$, and controls the knee joint torque $\tau$ in real time based on three impedance parameters: stiffness k, damping b, and equilibrium position $\vartheta_e$.

$$\tau_m = k_m(\theta - \theta e_m) + b_m\omega \tag{2}$$

Thus, with four gait phases, there are 12 total impedance parameters to be configured for each locomotion mode.

Representations of Knee Kinematics

Figure 5:
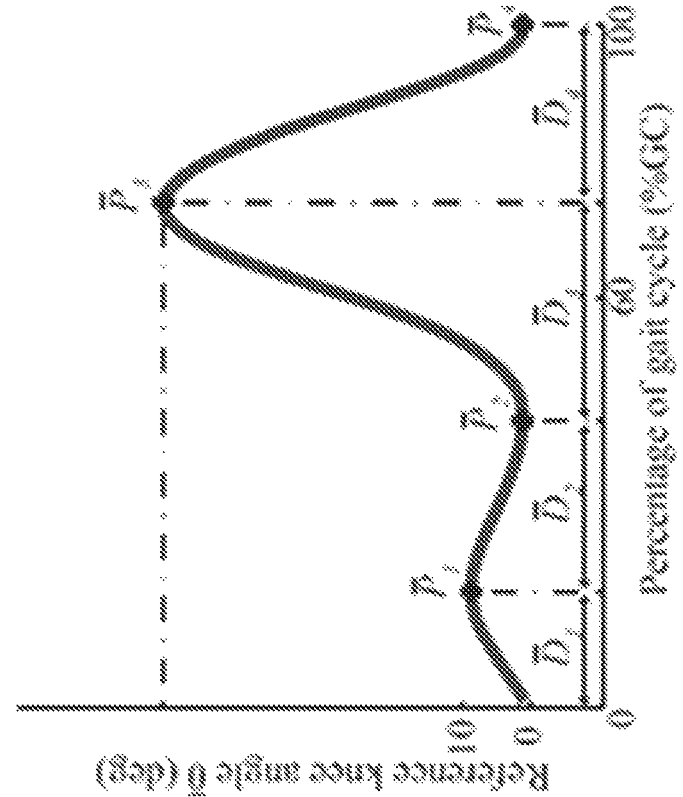
FIG. 5 is a graph illustrating feature representation of near-normal knee kinematics during one gait cycle was used as learning control target, where $\tilde{D}_m$ indicates the angle feature, and $\hat{P}_m$ indicates the duration feature. The phase index is indicated by m=1, 2, 3, 4. The start at 0%, and the finish at 100% are the heel strike events, and 60% is approximate toe off time.

Robotic knee kinematics are measured by an angle sensor mounted on the rotational joint. The angle sensor reads zero when the knee joint is extended to where the shank is in line with the thigh, and a positive value in degrees when the knee joint is flexed. Typically, the knee joint angle trajectory in one gait cycle has a local maximum during stance flexion and swing flexion, and a local minimum during stance extension and swing extension (FIG. 5). The peak value of each phase is primarily determined by the impedance parameters in that phase. Therefore, the knee kinematics in one gait cycle are represented with four pairs of peak angle values P and their respective duration values D: $[P_m, D_m]$, where m=1, 2, 3, 4. Similarly, the same features were extracted from normative knee kinematics as target features, denoted as $[\overline{P}_m, \overline{D}_m]$ (FIG. 5).

Human Prosthesis System Tuning Process

The tuning process is built upon the commonly-used FSM-IC framework, and the goal is to find a set of impedance parameters that allow the human-prosthesis system to generate normative target knee kinematics. As mentioned earlier, three impedance parameters took effect in each gait phase, and correspondingly, the knee kinematic features were extracted during each gait phase. For the ease of discussion, the subscript m is dropped for gait phase from hereon.

For the human-prosthesis system, the control inputs are the impedance parameters I(n), and the outputs are the features x(n) of prosthetic knee kinematics.

$$I(n) = [k(n), \theta e(n), b(n)]^T \tag{3}$$
$$x(n) = [P(n), D(n)]^T$$

where n denotes the index of each parameter update, which is every 7 gait cycles.

In the tuning procedure, the impedance parameters are updated as $$I(n) = I(n-1) + \beta \odot U(n-1), \tag{4}$$

where U denotes actions from the ADP-tuner, β∈R3×1 are scaling factors to assign physical magnitudes to the actions, and 8 is the Hadamard product of two vectors.

The states of the human-prosthesis system used in the learning controller are defined as $$X(n) = \gamma \odot \left[x^T(n) - \overline{x^T}, x^T(n) - x^T(n-1)\right]^T, \tag{5}$$

where $\gamma \in R^{4\times 1}$ is a vector of scaling factors to normalize the states to [−1, 1], and $\overline{x}$ are the features $[\overline{P}, \overline{D}]^T$ of the target knee kinematics. The feature errors $x(n)-\overline{x}$ capture the distance to the target knee kinematics, and the feature change rate x(n)−x(n−1) obtain the dynamic change during the tuning procedure.

In the tuning process, the actions from the ADP-tuner are adjustments to the impedance parameters, which are continuous, and the states to the ADP-tuner are derived from the features of knee kinematics, which are also continuous. Therefore, the human-prosthesis tuning process has continuous states and controls. Equations (3)-(5) are implemented in the "evaluation module" (FIG. 2) as an interface between the human-prosthesis system and the ADP-tuner. Additionally, the "evaluation module" includes reinforcement signals provided to the ADP-tuner based on the outputs of the human-prosthesis system.

The ADP Tuner

For the given human-prosthesis impedance parameter tuning problem, the ADP-tuner was implemented with four parallel dHDP blocks corresponding to four gait phases: STF, STE, SWF, and SWE (FIG. 2). Each dHDP block took in four state variables in (5) and tuned three impedance parameters for the respective phase. All dHDP blocks were identical, including one action neural network (ANN) and one critic neural network (CNN). Thus without loss of generality, we present the detailed dHDP implementation without phase numbers.

Utility Function/Reinforcement Signal

The reinforcement signal r(n)∈R is defined as the instantaneous cost that is determined from the human-prosthesis system.

$$r(n) = \begin{cases} -1, & \text{if } x(n) \notin [B_l, B_u] \\ -0.8, & \text{if } S^- > 4 \\ 0, & \text{otherwise} \end{cases} \tag{6}$$

where $[B_l, B_U]$ denotes the safety bounds as defined herein, $S^-$ is a penalty score, and the −0.8 reinforcement signal is imposed to the ADP block when the $S^-$ value is greater than 4, indicating the dHDP block continues to tune the impedance parameter in an unfavorable direction (i.e. increasing the angle error and/or duration error). When the reinforcement signal is −1, the impedance parameters of the human-prosthesis system are reset to default values.

The total cost-to-go at ADP tuning time step n is given by $$J(n) = r(n+1) + \alpha r(n+2) + \ldots + \alpha^N r(n+N+1) + \ldots \tag{7}$$

where α is a discount rate (0<α<1), and N is infinite. It can be rewritten as $$J(n) = r(n+1) + \alpha r(n+1). \tag{8}$$

Critic Neural Network

The CNN consisted of three layers of neurons (7-7-1) with two layers of weights, and it took the state $X \in R^{4\times 1}$ and the action $U \in R^{3\times 1}$ as inputs and predicted the total cost-to-go$\hat{J}$:

$$\hat{J}(n) = W_{c2}(n)\varphi\left(W_{c1}(n)\left[X^T(n), U^T(n)\right]^T\right), \tag{9}$$

where $W_{c1} \in R^{7\times7}$ was the weight matrix between the input layer and the hidden layer, and $W_{c2} \in R^{1\times7}$ was the weight matrix between the hidden layer and the output layer. And, $$\varphi(v) = \frac{1-\exp(-v)}{1+\exp(-v)} \tag{10}$$

$$v_{c1}(n) = W_{c1}(n)\left[X^T(n), U^T(n)\right]^T \tag{11}$$

$$h_{c1}(n) = \varphi(v_{c1}(n)) \tag{12}$$

where $\phi(\bullet)$ was the tan-sigmoid activation function, and $h_{c1}$ was the hidden layer output.

The prediction error $e_C \in R$ of the CNN can be written as $$e_c(n) = \alpha\hat{J}(n) - \left[\hat{J}(n-1) - r(n)\right]. \tag{13}$$

To correct the prediction error, the weight update objective was to minimize the squared prediction error $E_C$, denoted as $$E_c(n) = \frac{1}{2}(e_c(n))^2. \tag{14}$$

The weight update rule for the CNN was a gradient-based adaptation given by $$W(n+1) = W(n) + \Delta W(n). \tag{15}$$

The weight updates of the hidden layer matrix $W_{c2}$ were $$\Delta W_{c2}(n) = l_c(n)\left[-\frac{\partial E_c(n)}{\partial W_{c2}(n)}\right] = l_c(n)\left[-\frac{\partial E_c(n)}{\partial e_c(n)}\frac{\partial e_c(n)}{\partial \hat{J}(n)}\frac{\partial \hat{J}(n)}{\partial W_{c2}(n)}\right]. \tag{16}$$

The weight updates of the input layer matrix $W_{c1}$ were $$\Delta W_{c1}(n) = l_c(n)\left[-\frac{\partial E_c(n)}{\partial W_{c1}(n)}\right] = l_c(n)\left[-\frac{\partial E_c(n)}{\partial e_c(n)}\frac{\partial e_c(n)}{\partial \hat{J}(n)}\frac{\partial \hat{J}(n)}{\partial h_{c1}(n)}\frac{\partial h_{c1}(n)}{\partial v_{c1}(n)}\frac{\partial v_{c1}(n)}{\partial W_{c1}(n)}\right]. \tag{17}$$

where $I_C>0$ was the learning rate of the CNN.

Action Neural Network

The ANN consisted of three layers of neurons (4-7-3) with two layers of weights, and it took in the state $X \in R^{4\times1}$ from the human-prosthesis system and output the actions $U \in R^{3\times1}$ to adjust the impedance parameters of the human-prosthesis system:

$$U(n) = \varphi(W_{a2}(n) * \varphi(W_{a1}(n)X(n))), \tag{18}$$

where $W_{a1} \in R^{7\times4}$ and $W_{a2} \in R^{3\times7}$ were the weight matrices, and ¢ (•) was the tan-sigmoid activation function of the hidden layer and output layer.

Under the problem formulation, the objective of adapting the ANN was to backpropagate the error between the desired ultimate objective, denoted by $\bar{J}$, and the approximated total cost-to-go $\hat{J}$. And $\bar{J}$ was set to 0 indicating "success". Thus policy update goal was to minimize the absolute total cost-to-go value to 0. The weight update rule for the ANN was to minimize the following performance error:

$$E_a(n) = \frac{1}{2}\left(\hat{J}(n) - \bar{J}\right)^2. \tag{19}$$

Similarly, the weight matrix was updated based on gradient-descent:

$$W(n+1) = W(n) + \Delta W(n). \tag{20}$$

The weight updates of the hidden layer matrix $W_{a2}$ were $$\Delta W_{a2}(n) = l_a(n)\left[-\frac{\partial E_a(n)}{\partial W_{a2}(n)}\right]. \tag{21}$$

The weight updates of the input layer matrix $W_{a1}$ were $$\Delta W_{a1}(n) = l_a(n)\left[-\frac{\partial E_a(n)}{\partial W_{a1}(n)}\right]. \tag{22}$$

where $l_a>0$ is the learning rate of the ANN.

The above ANN and CNN weight updates and the ADP-tuner implementation is summarized in Algorithm 1. The weights of both ANN and CNN were initialized with uniformly distributed random numbers between −1 and 1. With mild and intuitive conditions, the dHDP with discounted cost has the property of uniformly ultimately boundedness (UUB).

---

Algorithm 1 On-line ADP-tuning of impedance parameters for robotic knee prosthesis

---

Initialization of human-prosthesis system: /(0), x(0), and
Random initialization of weights of ANN and CNN.
Step 1: Value update
Get state X(n) from (5) and reinforcement signal r(n) from (6)
Update weights of CNN using (13)-(17)
Step 2: Policy improvement
Update weights of ANN using (19)-(22).
Calculate U(n) from (18) and update I(n) using (4).
Reset I(n) if r(n) == −1 from (6).
Go to Step 1 until termination criteria (Section IV-E)

---

Design Considerations of Online Learning for Human Subjects

Human studies are different from simulation studies and therefore, the ADP-tuning algorithm was modified and implemented to accommodate real-life considerations for human subjects wearing a prosthetic leg.

Safety Bounds

For weight-bearing prostheses, safety is the primary concern, so constraints were included to ensure the human-prosthesis system outputs remain within a safe range (denoted by $[BI, B_U]$ in (6)). First, to avoid potential harm to an amputee user, bounds on the feature errors of 1.5 times the standard deviation of the average knee kinematic features of people walking without a prosthesis were set (i.e. STF 10.5 degrees, STE 7.5 degrees, SWF 9 degrees, SWE 6 degrees). Second, to avoid collision of mechanical parts in a prosthesis that may damage the robotic prosthesis, bounds on the range of motion to −5 degrees and 60 degrees were set. These constraints defined the exploration range for the ADP controller to avoid damage or harm to the human-prosthesis system. When the features exceeded these ranges, the control parameters were reset to the default values determined at the beginning of each experimental session, which were known to result in safe operation. At the same time, a −1 reinforcement signal was sent to the ADP-tuner.

Robust Feature Extraction

Sensor signal noise is inevitable from real prostheses, so a robust feature extraction method was implemented to extract features of the knee joint angle. In reality, the knee joint angle trajectory is not ideal mainly because of two reasons: 1) inevitable noise in the angle sensor readings, and 2) nearly flat angle trajectory at some places of a gait cycle where sensor readings remained steady. Under those conditions, the timing feature D varied greatly when obtaining the peak and duration values from a gait cycle. To address this, the minimum or maximum features [P̃i, D̃i] were first located from the knee joint angle trajectory, where i denotes sensor sample index (100 Hz). For each sample ϑj in the knee joint angle trajectory, there are two features [Pj, Dj]. The features at index j were selected to replace [P̃i, D̃i], where $$j = \operatorname{argmin}(D_j - \bar{D}), \tag{23}$$

and index j is within [i−10, i+10], and corresponding angle feature Pj is within [P̃i−0.3, D̃i+0.3]. This is to find robust and representative duration features based on real-time sensor measures.

Human Variability

To attenuate inevitable variations of human gait from step to step, the ADP-tuner processed the human-prosthesis system features every gait cycle, but control updates were made every seven gait cycles. This is to say, the human subjects walked with an updated set of impedance parameters for seven gait cycles. If the angle features of a particular gait cycle was greater than 1.5 standard deviations from the mean of the seven gait cycles, it was considered an outlier and removed. This eliminated accidental tripping or unbalanced gait cycles from influencing the control updates.

Prevention of Faulty Reinforcement Signals

As mentioned previously, the features of one gait phase impact the subsequent phases. To avoid propagating a faulty reinforcement signal, a −1 reinforcement signal only was provided to the dHDP block that exhibited out of bound angle/duration features. If multiple failure reinforcement signals were generated simultaneously, the feedback reinforcement signal was prioritized (from high to low) in the following order: STF, SWF, SWE, STE. In other words, if multiple phases generated −1 reinforcement signals in the same tuning iteration, the −1 reinforcement signal was applied to the dHDP block that had higher priority.

Termination Criteria

For practical applications with a human in the real-time control loop, termination criteria are necessary to avoid human fatigue in the tuning procedure. The tuning procedure was limited to 70 tuning iterations (i.e. 7×70=490 gait cycles) and terminated earlier if tuning was successful. Because human-prosthesis systems are highly nonlinear, vulnerable to noise and disturbances, and subject to uncertainty, a tolerance range μm (m=1, . . . , 4 denotes the four gait phases) was introduced for acceptable ranges of feature errors, which was 1.5 times the standard deviation of the features from more than 15 gait cycles without supplemental impedance control inputs. Parameter tuning in a given phase is considered successful if the features of this phase meet the tolerance criterion for at least three of the previous five tuning iterations. When all four phases are successful, the tuning procedure is considered a success and consequently terminated.

Experimental Design

Participants

One male able-bodied (AB) subject (age: 41 years, height: 178 cm, weight: 70 kg) and one male, unilateral transfemoral amputee (TF) subject (age: 21 years, height: 183 cm, weight: 66 kg, time since amputation: six years) were recruited. Both subjects provided written, informed consent before the experiments.

Prosthesis Fitting and Subject Training

A certified prosthetist aligned the robotic knee prosthesis for each subject. The TF subject used his own socket, and the AB subject used an L-shape adaptor (with one leg bent 90 degrees) to walk with the robotic knee prosthesis.

Each subject visited the lab for at least five 2-hour training sessions, including set up and rest time, to practice walking with our robotic knee prosthesis on an instrumented treadmill (Bertec Corp., Columbus, OH, USA) at 0.6 m/s. In the first training session, the impedance parameters were manually tuned based on the observation of the subject's gait and the subject's verbal feedback, similar to the tuning process in the clinic. In the second training session, a physical therapist trained the TF subject to reduce unwarranted compensation while walking with the robotic knee. The subjects were allowed to hold the treadmill handrails for balance when needed. The subject was ready for testing once he was able to walk comfortably for three minutes without holding the handrails.

Experimental Protocol

Three testing sessions (over three days) were conducted for each subject to evaluate the learning performance of a nave ADP, and an additional 4th testing session with the TF subject to evaluate performance of an experienced ADP in prosthesis tuning.

Initializing the ADP Tuner and Impedance Parameters

An ADP-tuner is nave if the ANN and the CNN were randomly initialized. An ADP-tuner is experienced if the ANN and the CNN were transferred from a previously successful session. Initial impedance parameters were randomly selected from a range obtained from previous experiments conducted on 15 human subjects, but the resulting knee motion was not optimized to the target. Initial parameter sets were skipped 1) did not allow the subject to walk without holding the handrails, 2) generated prosthesis knee kinematics that were too close to the target knee kinematics (i.e. root-mean-squared error (RMSE) between those two knee trajectories in one gait cycle was less than 4 degrees), or 3) generated knee kinematic features were out of the safety range.

Testing Sessions with Naïve ADP Tuner

In each of the three testing sessions, three minutes of acclimation time were first provided for the subject to walk with the newly initialized nave ADP-tuner and the control parameters. Then, the subject walked on the treadmill at 0.6 m/s for no more than 7 segments, each of which lasted no more than 3-minute walking periods. Each segment was followed by a 3-minute rest. These rest periods are typical in clinical settings, and they prevent potential confounding effects of fatigue. For all walking periods, the time series data of knee kinematics was recorded from the angle sensor and the loading force from the load cell.

The first 30 seconds of the first walking period served as our "pre-tuning" condition, in which the ADP-tuner was not enabled yet, and the impedance parameters remained constant (i.e. initial randomly-selected impedance parameters). The last 30 seconds of their final walking period served as our "post-tuning" condition for performance evaluation, in which the ADP-tuner was disabled and the impedance parameters were again held constant (i.e. the impedance parameters were at the final parameters provided by the ADP-tuner).

During all other walking periods, the subjects were asked to walk in a consistent manner on the treadmill while the ADP controller was enabled and iteratively updated the prosthesis impedance parameters. Each update (defined as ADP learning iteration) was performed every seven gait cycles. As said previously, this is to reduce step-to-step variability in the knee kinematics features of the peak angle and the phase duration. The ADP-tuner was paused during each rest period to prevent losing learned information.

The testing session was terminated when one of the two stop criteria were met: 1) the testing session reached 70 learning iterations to avoid subject fatigue, or 2) errors of all four angle features were within their corresponding tolerance range μ for three out of the previous five ADP learning iterations.

Testing Sessions with Experienced ADP Tuner

To evaluate if knowledge of the previously learned ADP-tuners would make learning more efficient, an additional testing session was conducted with the TF subject on another day with the same protocol. An experienced ADP, which used ANN and CNN network coefficients derived from the previous session that generated the lowest RMSE, was instead used at the start.

Data Analysis

The time-series robotic knee kinematics data were segmented into gait cycles based on the events of heel-strike (FIG. 5), and were then normalized to 100 samples per gait cycle.

The accuracy of the nave and experienced ADP-tuner was evaluated by the RMSE between measured and target knee kinematics and the feature errors obtained in each tuning iteration. To compare the pre-tuning and post-tuning performance, the averaged RMSE of knee kinematics and feature errors of 20 gait cycles in pre-tuning and post-tuning conditions were calculated and compared.

Data efficiency was quantified by the number of learning iterations in each testing session. Time efficiency was quantified by the subject's walking duration in each testing session.

Finally, the stability of the ADP-tuner was demonstrated by the tuned knee impedance parameters and knee kinematics (i.e. RMSE and feature errors averaged across 7 gait cycles within each iteration) across learning iterations.

Results

Figure 6:
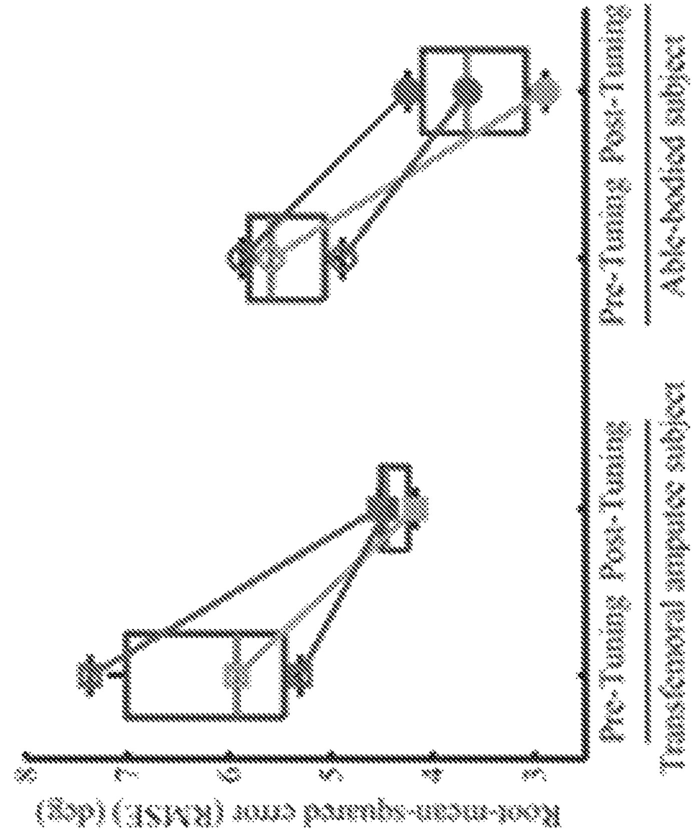
FIG. 6 illustrates a comparison of knee kinematics by RMSE between pre-tuning and post-tuning across multiple testing sessions. The square markers represent the testing sessions from the TF subject, and circle markers represent the testing sessions from AB subject. Open marker represents the pre-tuning condition, and closed marker represents the post-tuning condition.
Figures 7A, 7B:
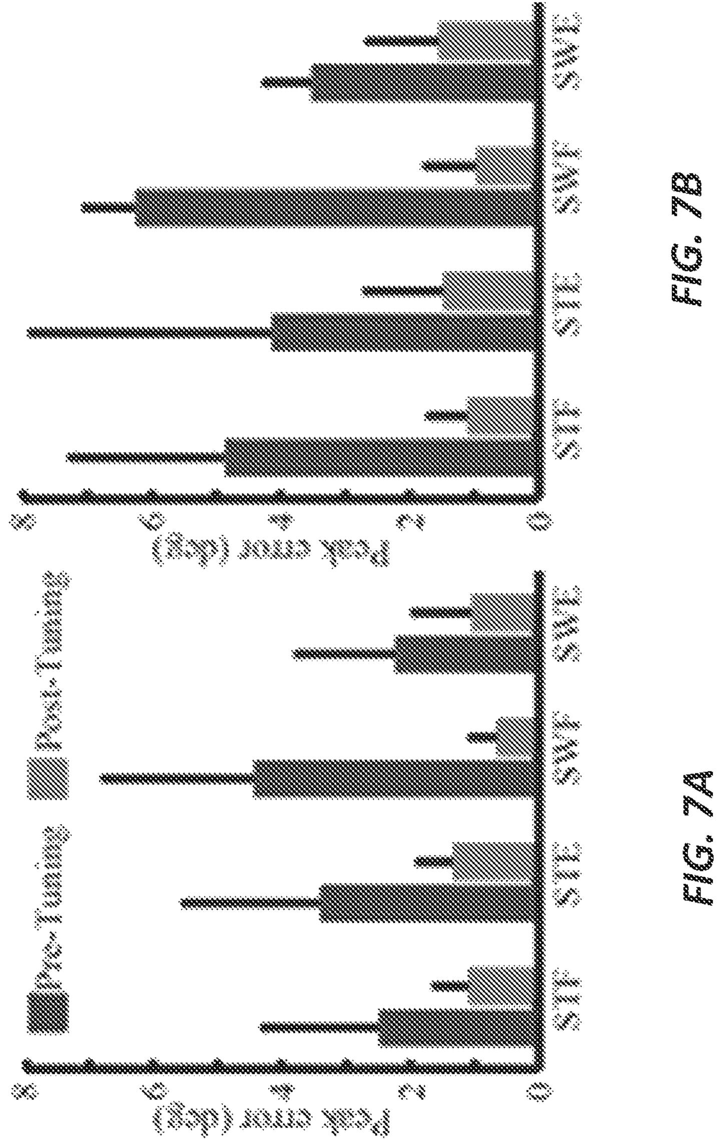
FIGS. 7A-7B are graphs illustrating peak error comparison between pre-tuning and post-tuning conditions of the TF subject (FIG. 7A), and the AB subject (FIG. 7B) at each phase. Each bar represents the mean error of three testing sessions, and the error bars denote one standard deviation from the mean.

As a measure of accuracy of the ADP-tuner, the RMSE of the robotic knee angle (compared to the target) averaged across testing sessions and subjects decreased from 5.83±0.85 degrees to 3.99±0.62 degrees (FIG. 6, individual subject results). All the angle feature errors decreased after tuning by the ADP-tuner (FIGS. 7A-7B). The duration feature errors did not show a consistent trend (FIGS. 8A-8B) across these two subjects. This variability of the duration feature errors was no surprise because 1) the duration of each phase is partially controlled by the human prosthesis user, and 2) the ADP algorithm allowed more flexibility (or relatively larger acceptable range) of the duration feature errors than the angle feature errors to meet the target and complete tuning.

Figures 12A, 12B, 12C, 12D:
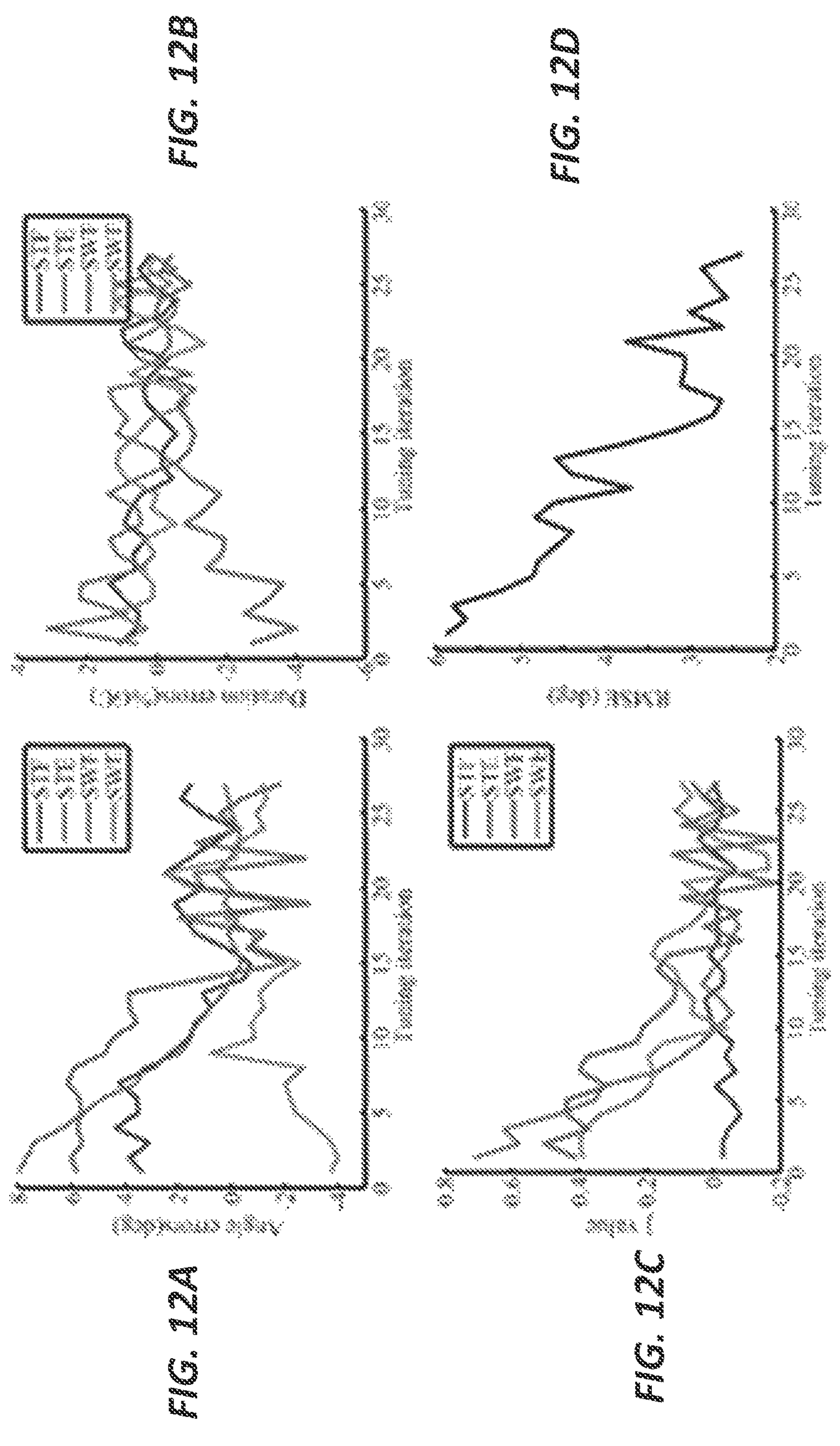
FIGS. 12A-12D are graphs illustrating learned ADP autotuner on-line evaluation results.
Figures 14A, 14B, 14C, 14D:
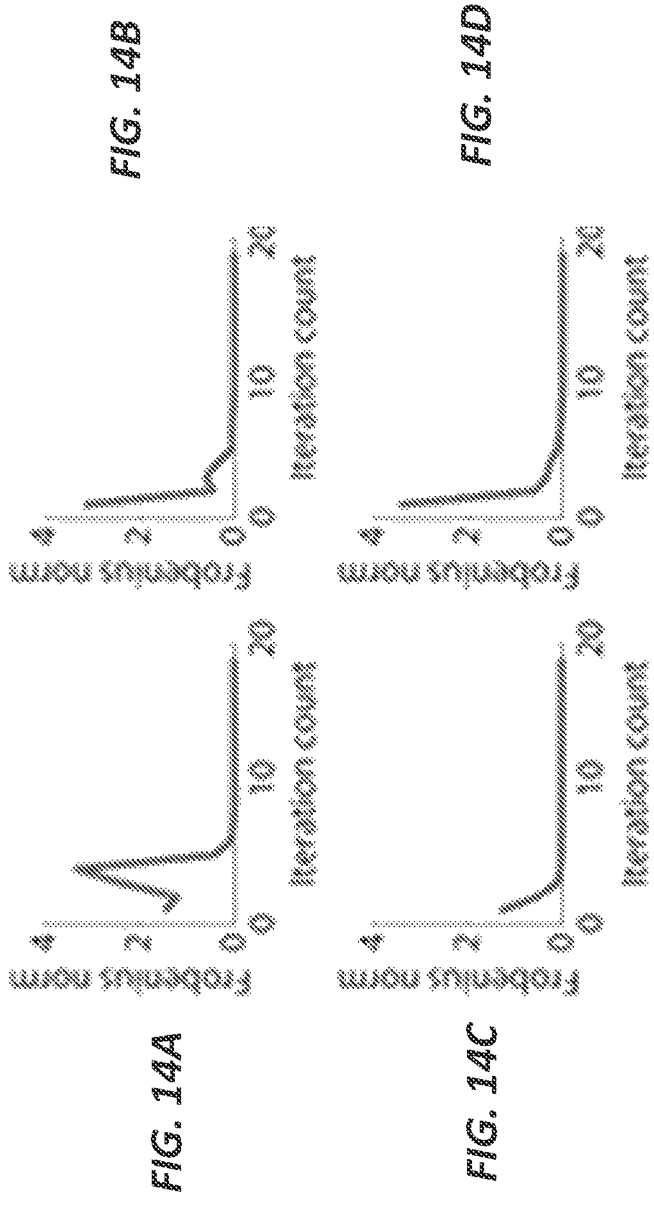
FIGS. 14A-14D are graphs illustrating the Frobenius norm of the difference between two successive S matrices which vary as the policy iteration number increases for the four different phases.

As measures of data and time efficiency, the ADP-tuner took an average of 43±10 learning iterations to find the "optimal" impedance parameters, amounting to an average of 300 gait cycles and 10±2 minutes of walking. The data and time efficiency were similar between subjects (able-bodied: 45±9 iterations, amputee subject: 41±12 iterations). Both the feature errors and impedance parameters generally stabilized by the post-tuning period (FIGS. 9A-9D and FIGS. 10A-10D, representative trial shown). In particular, both the feature errors and the impedance parameters of the swing flexion and swing extension gait phases stabilized. However, for stance flexion and stance extension, the feature errors stabilized, while the impedance parameters were still changing slowly. The final impedance parameters that the ADP-tuner selected to allow the user to walk with a near-normal knee motion, or the target knee profile, were not the same across all testing sessions (Table I, FIG. 11). In general, the stiffness parameters and damping parameters at stance phases (2.33±0.56 Nm/deg, 0.13±0.05 Nms/deg) were greater than those of the swing phases (0.95±0.83 Nm/deg, 0.03±0.02 Nms/deg). In the experienced ADP test session, for all four gait phases, both the angle and duration feature errors followed a decreasing trend toward zero (FIGS. 12A and 8 12B). The $\hat{J}$ value of the CNN network decreased along the tuning iteration (FIG. 12C), and the RMSE of the robotic knee kinematics decreased from 5.9 degrees to 2.5 degrees from pre- to post-tuning (FIG. 12D). In this case evaluation, the experienced ADP-tuner took 28 iterations (approximately 7 minutes) to find the 12 'optimal' impedance parameters. No additional reinforcement signal occurred during this testing session with the experienced/learned ADP.

Discussion

This example demonstrates the feasibility of a RL-based approach for personalization of the control of a robotic knee prosthesis. A total of 12 impedance parameters were tuned simultaneously using the ADP-tuner described herein for two human subjects.

Feasibility and Reliability

The accuracy of ADP-tuner to meet the target knee angle profile both for each gait phase (FIGS. 7A-7B and FIGS. 8A-8B) and the entire gait cycle (FIG. 6) indicates that the ADP-tuner was feasible to optimize a large number of prosthesis control parameters. In this example, the ADP-tuners adjusted impedance parameters allowed both subjects to walk consistently towards near-normal knee kinematics.

In addition, the ADP-tuner reliably reproduced similar results for all testing sessions, each of which began with different, randomly-initialized ANN and CNN weight matrices (i.e. no prior knowledge built into the learning controller) and impedance parameters.

Variations in the final impedance parameters after ADP tuning indicated that multiple combinations of impedance parameters yielded similar prosthesis kinematics (Table I, FIG. 11). This is not surprising because according to (2), the motor torque is underdetermined by a combination of three impedance parameters.

Figures 8A, 8B:
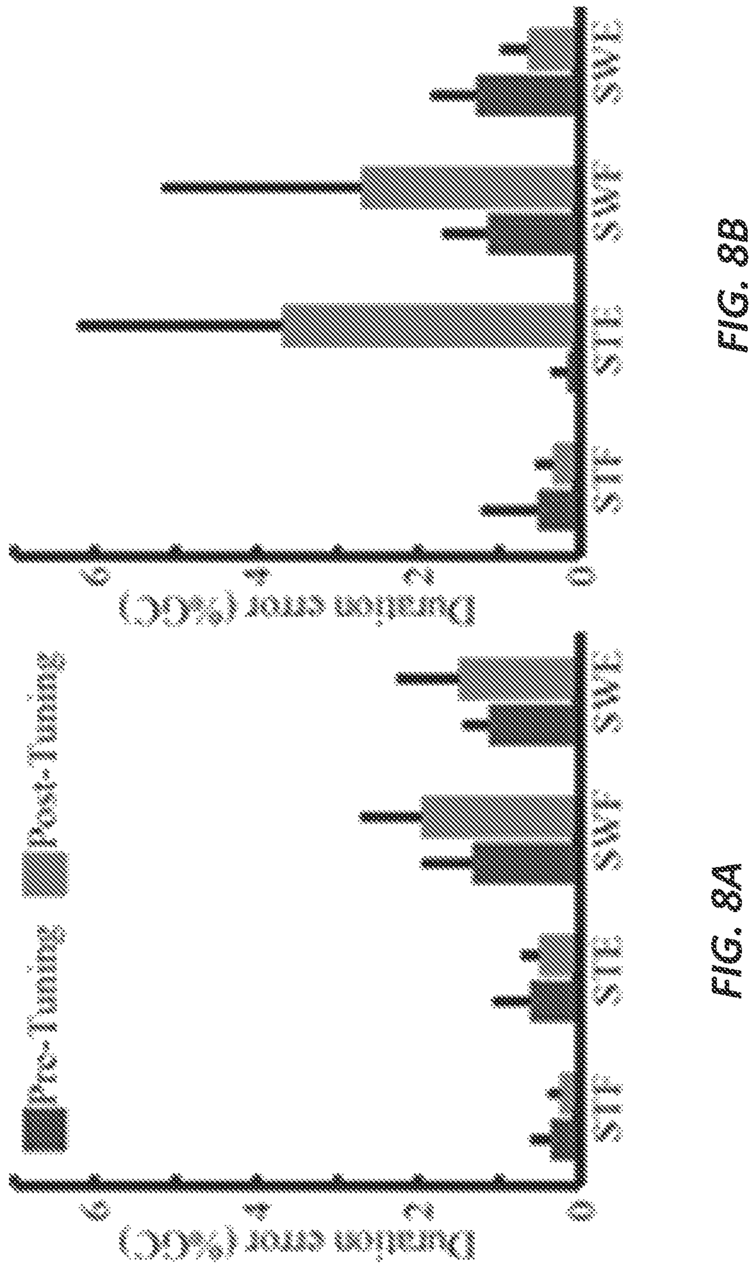
FIGS. 8A-8B are graphs illustrating duration error comparison between pre-tuning and post-tuning conditions of the TF subject (FIG. 8A) and the AB subject (FIG. 8B) for each phase. Each bar represents the mean error of three testing sessions, and the error bars denote one standard deviation from the mean.
Figures 9A, 9B, 9C, 9D:
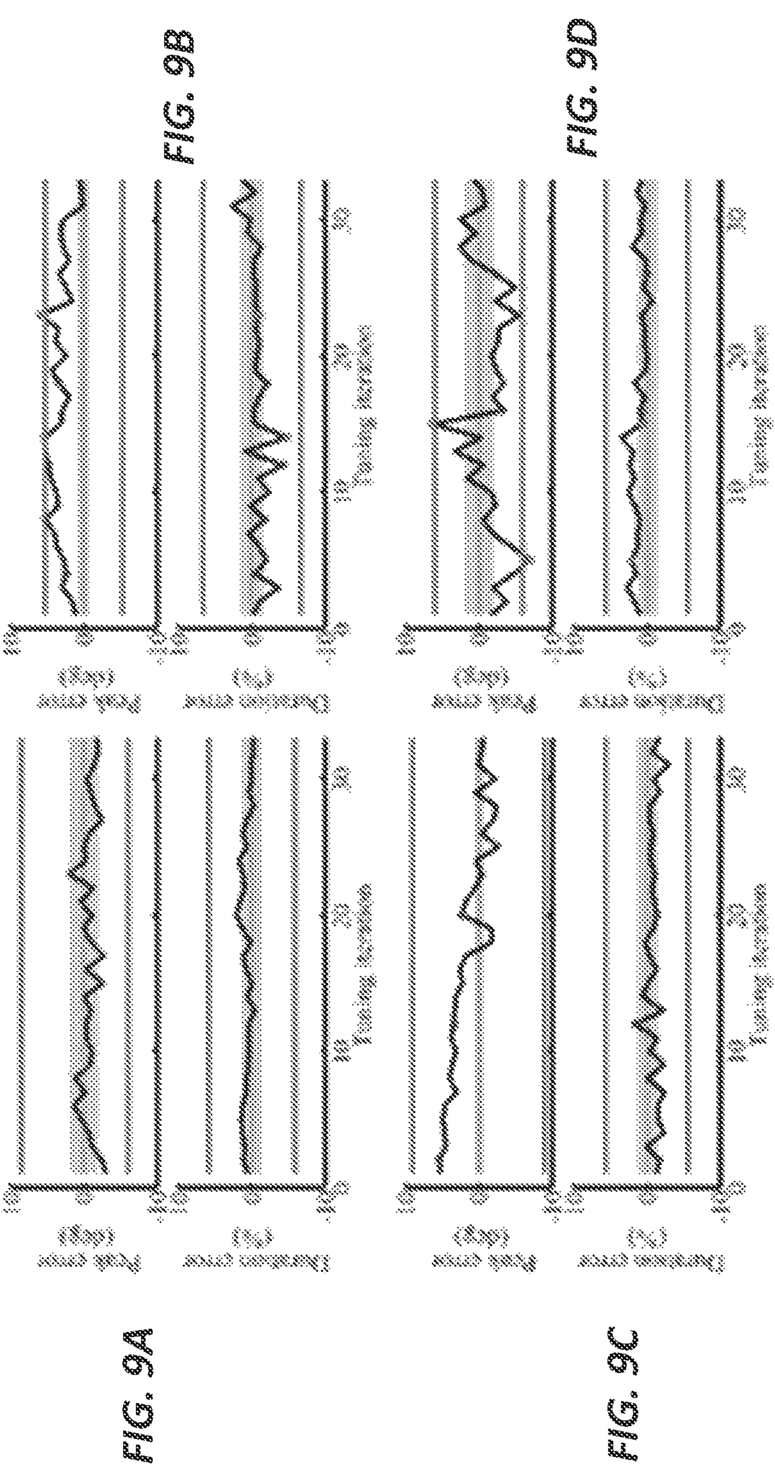
FIGS. 9A-9D are graphs illustrating peak error and duration error during the four phases for a representative tuning procedure.
Figures 10A, 10B, 10C, 10D:
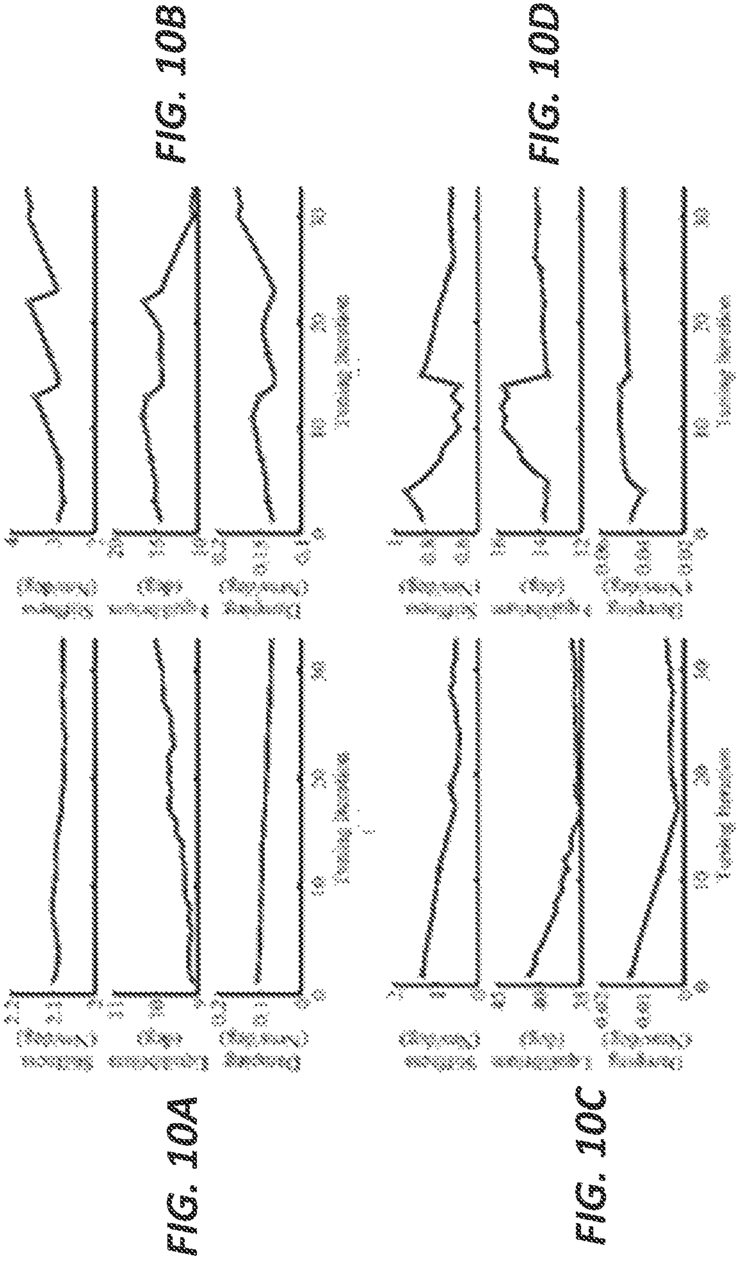
FIGS. 10A-10D are graphs illustrating impedance parameters of the four phases during a representative tuning procedure.

Even though the prosthetic knee kinematics were solely measured from the prosthesis, it represented an inherently combined effort from both the human and the machine or the prosthesis controller. Based on the results, the robotic knee flexion/extension peaks are primarily influenced by the impedance parameters and thus affected by our ADP-tuner (FIGS. 7A-7B), but the duration of each gait phase may be dominated by the human user (FIGS. 8A-8B). Subjects were able to control the timing of their gait events likely because they can control when to place and lift the prosthetic foot on or off the treadmill with their ipsilateral hip and entire body. In the feedback control of robotic prostheses, the feedback signals must be responsive to the control action. Therefore, using knee kinematics as the feedback and optimization state was reasonable.

Efficiency

Starting without any prior knowledge or a plant model, the ADP-tuner described herein was able to gather information and gain understanding on how to simultaneously tune the 12 control parameters in 10 minutes of one test session, or 300 gait cycles for both subjects. As a reference, an advanced expert system tuning method required at least three days of systematic recording of a human experts tuning decisions and transferred those knowledge to a computer algorithm (see e.g., U.S. Pat. No. 10,335,294, issued Jul. 2, 2019), which then took 96 gait cycles to tune the impedance parameters. Note however, this cyber-expert system is subjective (i.e. biased by prosthetists experience) and inflexible when the system input and output changes. The ADP-tuner described herein is objective and flexible in structure. Furthermore, the experienced ADP-tuner (i.e. with some prior knowledge) took only 210 gait cycles without additional reinforcement signals to learn, demonstrating the learned knowledge can be effectively transferred to tune the impedance parameters. Therefore, the ADP-tuner is time and data efficient for clinical use.

In daily life, the ADP-tuner potentially can handle slow changes, such as body weight change. For environmental demand changes, like going from level ground walking to walking up a ramp or stair, the ADP-tuner could potentially find the "optimal" control parameters for each locomotion modes (e.g. ramp walking, stair climbing), which might take longer, but could store the impedance parameters and switch the parameters when the user encounters task changes in real life.

Learning Outcome

The ADP-tuner learned through reinforcement signals (FIGS. 9A-9D and FIGS. 10A-10D, colored point characters) and was able to tune impedance parameters that in turn decreased the angle feature errors to meet the respective error tolerance. At the end of the tuning procedure, the feature errors also maintained within the tolerance range for at least three of the previous five ADP learning iterations in order to terminate the tuning session.

The feature errors clearly converged toward zero in two out of four phases (FIG. 9C and FIG. 9D), and the corresponding impedance parameters (FIG. 10C and FIG. 10D) stabilized. These results demonstrate that the ADP-tuner is able to generate a converged policy for these gait phases. However, in the remaining two phases, the impedance parameters were still adapting, but the feature errors were within the tolerance ranges. These results lead one to believe the feature errors may not be very responsive to certain impedance parameters or combinations of parameters. This phenomenon may be also caused by stop criteria of maximum 70 tuning iterations, enforced to keep this study practical for clinical applications and to prevent amputee from fatigue. To achieve a converged policy quickly, this challenge can be addressed by adding small disturbances to the impedance parameters when the feature errors approach zero in order to test convergence properties of the ADP-tuner and by allowing ADP-tuner to accumulate more learning experiences.

Finally, the experienced ADP-tuner described herein demonstrated, after only interacting with the human-prosthesis system for one testing session, effectively learned tuning knowledge to reach the target knee kinematics. With both human and inter-phase influence contributing to the robotic knee motion, both the angle and duration feature errors were expected to oscillate about zero (FIG. 12A and FIG. 12B). In addition, the experienced ADP tuned the prosthesis control parameters faster than the nave ADP. This exciting result opens up the opportunity to make the prosthesis controller adaptive to users in their daily life.

Implications of Results

In this example, the ADP-tuner had no prior knowledge of 1) the structure of the impedance controller and 2) the mechanical properties of the robotic knee prosthesis. The only information observed by the ADP was the state of the human-prosthesis system through measurements of the prosthetic knee angle, and reinforcement signals when the performance/features were out of allowed exploration range. Therefore, the ADP-tuner design can be applied to knee prostheses with different mechanical structures and control methods and even possibly extended to the control parameter tuning problem for ankle prostheses and exoskeletons.

Further, the ADP-tuner described herein may be applied to other control objectives to reach behavioral goals. For example, if the target knee kinematics is to generate a greater swing flexion angle for foot clearance, the experienced ADP-tuner may potentially tune the impedance parameters quickly to reach the new target. Therefore, the learned control policy may significantly enhance the tuning/personalization process of robotic prostheses, as well as the adaptability of the prosthesis to changes within a user and its environment.

CONCLUSION

In this study, a significant leap forward from the traditional time-consuming and labor-intensive manual tuning of the prosthesis control parameters is provided. In particular, an RL-based control approach to automatically tune 12 impedance parameters of a robotic knee prosthesis was developed. The concept was validated on one able-bodied subject and one transfemoral amputee through multiple testing sessions. The results illustrated that the ADP-tuner is a feasible and safe method to automatically configure a large number of control parameters within the scope of this study. The algorithm learns efficiently through interaction with the human-prosthesis system in real time, without any prior tuning knowledge from either a trained clinician or a field expert. The learning also does not require a prior plant model of the human-prosthesis system.

Example 2: Offline Reinforcement Learning Control

This example aims to develop an optimal controller that can automatically provide personalized control of robotic knee prosthesis in order to best support gait of individual prosthesis wearers. A reinforcement learning (RL) controller is introduced for this purpose based on the promising ability of RL controllers to solve optimal control problems through interactions with the environment without requiring an explicit system model. However, collecting data from a human-prosthesis system is expensive and thus the design of a RL controller has to take into account data and time efficiency. An offline policy iteration based reinforcement learning approach is described below. This solution is built on the finite state machine (FSM) impedance control framework, which is the most used prosthesis control method in commercial and prototypic robotic prosthesis. Under such a framework, an approximate policy iteration algorithm was designed to devise impedance parameter update rules for 12 prosthesis control parameters in order to meet individual users' needs. The goal of the reinforcement learning-based control was to reproduce near-normal knee kinematics during gait. The RL controller obtained from offline learning was tested in real time experiment involving the same able-bodied human subject wearing a robotic lower limb prosthesis. The results showed that the RL control resulted in good convergent behavior in kinematic states, and the offline learning control policy successfully adjusted the prosthesis control parameters to produce near-normal knee kinematics in 10 updates of the impedance control parameters.

The robotic prosthesis industry has experienced rapid advances in the past decade. Compared to passive devices, robotic prostheses provide active power to efficiently assist gait in lower limb amputees. Such active devices are potentially beneficial to amputees by providing the capability of decreased metabolic consumption during walking, improved performance while walking on various terrains, enhanced balance and stability, and improved adaptability to different walking speed. In term of control for robotic prostheses, although several ideas have been proposed in recent years, the most commonly used approach in commercial and prototypic devices is still the finite state machine (FSM) impedance control.

The FSM impedance control framework requires customization of several impedance parameters for individual users in order to accommodate different physical conditions. This requirement currently poses a major challenge for broad adoption of the powered prosthesis devices because of the following reasons. For robotic knee prosthesis, the number of parameters to be configured is up to 15. However, in clinical practice, only 2-3 parameters are practically feasible to be customized by prosthetists manually and heuristically. This procedure is time and labor intensive. Researchers have attempted alternative ways to manual tuning. To mimic the impedance nature of biological joint, intact leg models were studied to estimate the impedance parameters for the prosthetic knee joint. Yet, the accuracy of these models have not been validated. A cyber expert system approach to finding the impedance parameters has been developed (see e.g., U.S. Pat. No. 10,335,294, issued Jul. 2, 2019). Most recently, some studies proposed to take into account the human's feedback in the optimization for the parameter configuration and demonstrated the promise. However, these methods still have some limitations, such as hard to extend for configuring high dimensional parameters or imposing a prerequisite on the dataset which has to cover all users' preference.

In fact, the process of configuring impedance parameters can be formulated as a control problem of solving optimal sequential decisions. Because of the ability to autonomously learn an optimal behavior through interactions rather than explicitly formulate a detailed solution to a specific problem, the reinforcement learning (RL) based control design becomes a natural candidate when it comes to addressing the aforementioned challenges of configuring robotic knee prosthesis to meet individual needs. Recently, RL was successfully applied to solving robotic problems that involve sophisticated and hard-to-engineer behaviors. In most of these successful applications, policy search methods were at the center of the development. For example, Gu developed an off-policy deep Q-function based RL algorithm to learn complex 7 DoF robotic arm manipulation policies from scratch for a door opening task. Vogt presented a data-driven imitation learning system for learning human-robot interactions from human-human demonstrations. However, deep RL based methods may not be appropriate in some biomedical applications such as the human-prosthesis control problem under consideration.

One primary reason is that training data involving human subjects are usually not easily acquired or expensive to collect. Additionally, experimental session involving human subjects usually cannot last more than one hour because of human fatigue and safety considerations. Putting it together, we are in need of a reinforcement learning controller that can adapt to individual conditions in a timely and data efficient manner.

An actor critic RL controller, namely direct heuristic dynamic programming (dHDP) to the robotic knee prosthesis parameter tuning problem, is described above in Example 1. By interacting with the human-prosthesis system and under the same FSM impedance control framework, dHDP learned to reproduce near-normal knee kinematics. It took about 300 gait cycles or about 10 minutes of walking to achieve acceptable walking performance. Moreover, because it is an online learning algorithm, it has not been developed to take advantage of existing offline data.

To this end, an approximate policy iteration based reinforcement learning controller is introduced in Example 2. Compared to the previous dHDP approach of Example 1, policy iteration has several advantages. First, it enjoys several important properties of classic policy iteration algorithm such as convergent value functions and stable iterative control policies. Second, it is reported that policy iteration has higher data and time efficiency than general gradient descent based methods. Third, the policy iteration based RL approach can learn from offline data to fully utilize historical data. As such, this learning controller can potentially be expanded to solve more complex problems that require an integration of both online and offline data.

The objective of this example is to develop and evaluate the feasibility of a policy iteration based learning control for personalizing a robotic prosthesis. The real human-prosthesis system is rich in unmodeled dynamics and uncertainties from environment and human. Especially, the human variances and consequent impact on the prosthetic knee and the human-prosthesis system have made controlling the robotic prosthesis more challenging than those problems encountered in humanoid robots or human-robot interactions to jointly perform a task such as picking up a box. This is because the human-prosthesis system interact and evolve seamlessly at an almost instantaneous time scale, i.e., a potentially out-of-control parameter adjustment in the prosthesis can result in system instability almost immediately, which is much less tolerant than a human-robot system.

In this paper, a reinforcement learning controller realized by approximate policy iteration was successfully designed to control robotic lower limb prosthesis with human in the loop. This prosthesis control design approach is data efficient as it was derived from offline data collected from interactions between human and prosthesis. This learning controller was demonstrated for tuning 12 prosthesis parameters to approach desired normal gait on real human subject.

Human Prosthesis Integrated System

Finite Machine Framework

FIGS. 3A-3C illustrate reinforcement learning controlled prosthesis in a human-prosthesis integrated system. The learning controller is realized within a well established FSM platform. Specifically, an FSM partitions a gait cycle into four sequential gait phases based on knee joint kinematics and ground reaction force (GRF). These four gait phases are stance flexion (STF), stance extension (STE), swing flexion (SWF) and swing extension (SWE). In real-time experiments, transitions between phases are realized based on Dempster-Shafer theory (DST). For each phase, the prosthetic system mimicked a passive spring-damper-system with predefined impedance that matched the biological knee impedance. The predefined impedance parameters are selected by the finite state machine and outputted to the impedance controller as $$I = [K, B, q_e]^T \hat{I}_1^3, \tag{24}$$

where K is stiffness, B is damping coefficient and $\vartheta_e$ is equilibrium position. In other words, for all four phases there are 12 impedance parameters to activate the knee joint which directly impact the kinematics of the robotic knee and thus the performance of the human-prosthesis system. The knee joint torque $T\hat{I}_i$ is generated based on the impedance control law $$T = K(q - q_e) + Bw. \tag{25}$$

The four target points (red markers) in the dashed plot and four control points (black markers) in the solid plot of FIG. 3C provide state information for the learning controller to generate optimal control. The chosen points were the maximum or minimum points within each phase, so they could characterize basic knee movements. To approach the normal gait, target points were set to resemble the corresponding points in normative knee kinematics measured in able-bodied individuals.

Specifically, one learning controller is designed for one phase under the FSM framework. Without loss of generality, our following discussion involves only one of the four phases. In each phase, peak error $DP\hat{I}_i$ and duration error $DD\hat{I}_i$ are defined as the vertical and horizontal distance between the corresponding pair of control point and target point. Then the state x of the RL controller are formed using $DP\hat{I}_i$ and $DD\hat{I}_i$ as $$x = [DP, DD]^T. \tag{26}$$

Correspondingly, the action u is the impedance adjustment DI, $$u = DI. \tag{27}$$

Additional insights and construct on the FSM framework and the peak/duration errors can be found in Wen et al.

Offline Reinforcement Learning Control Design

Problem Formulation

In this example, the integrated human-prosthesis system was considered as a discrete-time nonlinear system (28), $$x_{k+1} = F(x_k, u_k), k = 0, 1, 2, \tag{28}$$

$$u_k = \pi(x_k) \tag{29}$$

where k is the discrete time index that provides timing for each impedance control parameter update, $x_k \in \mathbb{R}^2$ is the state vector x at time k, $u_k \in \mathbb{R}^2$ is the action vector u at time k, F is the unknown system dynamics, and $\pi$: $\mathbb{R}^2 \rightarrow \mathbb{R}^3$ is the control policy.

To provide learning control of the prosthesis within system (28), we formulate an instantaneous cost function $U_{(x,u)}$ in a quadratic form as $$U(x, u) = x^T R_x x + u^T R_u u \tag{30}$$

where $R_x \in \mathbb{R}^{2\times 2}$ and $R_u \in \mathbb{R}^{3\times 3}$ are positive definite matrices. We use (30) to regulate state x and action u, as larger peak/duration error as in (26) and larger impedance adjustment as in (27) will be penalized with a larger cost.

The infinite horizon cost function $Q(x_k,u)$ is defined as $$Q(x_k, u) = U(x_k, u) + \sum_{j=k+1}^{\infty} \gamma^{j-k} U(x_j, \pi(x_j)) \tag{31}$$

where g is a discount factor. Note that the $Q(x_k,u)$ represents the cost function when action u is applied at state $x_k$, the system (28) then reaches $x_{k+1}$ and follows the control policy $\pi$ thereafter.

The optimal cost function $Q^*(x_k, u)$ satisfies the Bellman optimality equation $$Q^*(xk, u) = U(xk, u) + \gamma Q^*(xk+1, \pi^*(xk+1)) \tag{32}$$

where the optimal control policy $p^*(x_k)$ can be determined from $$p^*(x_k) = \underset{u}{\text{argmin}} Q^*(x_k, u) \quad (33)$$

Policy iteration is used to solve the Bellman optimality equation (32) iteratively in this study. Policy iteration has several favorable properties such as convergence guarantee and high efficiency, which make it a good candidate for configuring a robotic knee with human in the loop. Starting from an initial admissible control $p^{(0)}(x_k)$, the policy iteration algorithm evolves from iteration i to i+1 according to the following policy evaluation step and policy improvement step. Note that for offline training, a zero output policy is sufficient to be an initial admissible control.

Policy Evaluation $$Q^{(i)}(x_k, u) = U(x_k, u) + \gamma Q^{(i)}(x_{k+1}, \pi^{(i)}(x_{k+1}))\ i = 0, 1, 2 \ldots \quad (34)$$

Policy Improvement $$\pi^{(i+1)}(x) = \underset{u}{\text{argmin}} Q^{(i)}(x, u),\ i = 0, 1, 2, \quad (35)$$

Equation (34) performs an off-policy policy evaluation, which means the action u need not to follow the policy being evaluated. In other words, $u^1\ p^{(i)}(x_k)$ in general. This makes it possible to implement (34) and (35) in an offline manner using previously collected samples and thus achieve data efficiency. Solving (34) and (35) requires exact representations of both cost function and control policy, which is often not tractable in robotic knee configuration problem where continuous state and continuous control are involved. This issue is circumvented by finding an approximated solution for (34) using offline data.

Offline Approximate Policy Iteration

For implementation of the policy evaluation equation (34), a quadratic function approximator is used to approximate the cost function $Q^{(i)}(x,u)$ in the i th iteration as $$\hat{Q}^{(i)}(x, u) = \begin{bmatrix} x \\ u \end{bmatrix}^T S^{(i)} \begin{bmatrix} x \\ u \end{bmatrix} = \begin{bmatrix} x \\ u \end{bmatrix}^T \begin{bmatrix} S_{xx}^{(i)} & S_{xu}^{(i)} \\ S_{ux}^{(i)} & S_{uu}^{(i)} \end{bmatrix} \begin{bmatrix} x \\ u \end{bmatrix} \quad (36)$$

where $S^{(i)} \in \mathbb{R}^{5\times 5}$ is a positive definite matrix and $$S_{ux}^{(i)}, S_{xx}^{(i)}, S_{xu}^{(i)} \text{ and } S_{uu}^{(i)}$$

are submatrices of $S^{(i)}$ with proper dimensions. The quadratic form of (36) corresponds to the instantaneous cost function U(x,u) in (30).

To utilize offline data with the approximated cost function (36), samples are formulated as 3-tuples $$(x_n, u_n, x_n'),\ n = 1, 2, 3 \ldots N,$$

where n is the sample index and N is the total number of samples of the offline dataset.

The 3-tuple $$(x_n, u_n, x_n^¢)$$

means that after control action $u_s$ is applied at state $x_n$, the system reaches the next state $$x_n^¢.$$

In other words, $$x_n \xrightarrow{u_n} x'_n$$

is required to formulate a sample, but $$x_n^¢$$

needs to be equal to $x_{n+1}$, $u_{n+1}$ does not need to be on-policy, i.e. following a specific policy. specific policy. Notice that k represents a sequential time evolution associated with gait cycle, but n does not need to follow such an order because offline sample n and n+1 may come from two different trials. Hence, collecting offline samples is much more flexible than collecting online learning samples. Having an offline dataset D=

$$\{(x_n, u_n, x_n'),\ n = 1, 2, 3 \ldots N\},$$

following approximate policy evaluation step can be performed according to (34), $$\hat{Q}^{(i)}(x_n, \mu_u) = U(x_n, u_n) + g\hat{Q}^{(i)}(x_n^¢, p^{(i)}(x_n^¢)) \quad (37)$$

Solving (37) for $\hat{Q}^{(i)}(x_n,u_n)$ is equivalent to solving for $S^{(i)}$. In other words, based on (36), the policy evaluation (37) can be converted to the following convex optimization problem with respect to $S^{(i)}$, $$\text{minimize } m_h^T S^{(i)} m_k - g(m_k^¢)^T S^{(i)} m_h^¢ - U(m_h) \quad (38)$$
$$\text{subject to } S^{(i)}\ f\ 0$$

where $$m_n = \left[x_n^T, u_n^T\right]^T \text{ and } m_n^¢ = \left[x_n^{¢T}, p^{(i)}(x_n^¢)^T\right]^T.$$

After obtaining the $S^{(i)}$ and $\hat{Q}^{(i)}(x_n,u_n)$, policy can be updated based on $$p^{(i+1)}(x_n) = \underset{u_n}{\operatorname{argmin}} \hat{Q}^{(i)}(x_n, u_n) \tag{39}$$

which is an approximate version of (35). In practice, constraints on actions are added to keep actions within a reasonable range (TABLE I, FIG. 13). As a result, policy update (39) can be converted to a quadratic programming problem, $$\begin{aligned} &\text{minimize } \hat{Q}^{(i)}(x_n, u_n) \\ &\text{subject to } u_{-} \text{″} u_n \text{″} u_{+} \end{aligned} \tag{40}$$

where u− and u+ are the lower bound and upper bound of acceptable action, respectively. The values of u− and u+ can be found in TABLE I. Convex optimization cam be used to solve (38) and (40).

Algorithm 1 in FIG. 13 summarizes the implementation of the offline approximate policy iteration algorithm.

Implementation of Offline Policy Training

The offline training data including N=140 pairs of the $$(x_n, u_n, x_n^c)$$

tuples came from two separate experiments involving the same human subject using the same prosthesis device. The whole data collection process took 29 minutes to complete. During data collection, the prosthesis impedance parameters were controlled by the dHDP based RL approach that was investigated previously. Note, however, that the dHDP was used to only provide some control to the prosthesis or in other words, dHDP was an enabler of the data collection session. That is to say that the data were drawn from the online learning process of the dHDP RL controller rather than generated by a well-learned policy. During data collection, the state $x_n$ and next state $$x_n^c$$

in each pair of sampled tuples were averaged by 7 gait cycles conditioned on the same action $u_n$. In addition, prior to applying Algorithm 1, all samples were normalized into the range between −1 and 1 to avoid ill-conditioning issues during application of convex optimization to achieve admissible control policies.

The discount factor g was set to 0.8. The termination condition of the Algorithm 1 in FIG. 13 was set as a maximum of $i_{max}$=100 iterations. The weight matrices of state and action were specified as $R_x$=diag(10,1) and $R_u$=diag(1,1,1), respectively. They were specified to make the peak error dominating the cost. Because, compared to the duration error which is partially controlled by human behaviors (e.g. heel-strike or toe-off timing), the peak error is more sensitive to the parameter changes. Moreover, as a factor determining gait performance, the peak error is more important than the action taken in our settings. Yet, the duration error still needs to be taken as one of the monitored states in the controller, because the controller has to adjust parameters to keep the duration error in a reasonable range. Otherwise, human users cannot stabilize the duration error by themselves.

To evaluate the convergence of the trained policies, the changes of S matrix in the approximate cost function $\hat{Q}$ was investigated over the entire offline training process for each phase. As a measure of element-wise distance regarding two matrices, the Frobenius norm of the difference between two successive matrices $\|S^{(i+1)}-S^{(i)}\|_F$ was adopted to quantify the changes. As FIGS. 14A-14D show, the norm value of the difference reduced fast when the training process started off for each phase, and they all approached zeros within 10 iterations. The result indicates that the approximated cost function as well as the policy was convergent and optimal given the training dataset. It took about 5 minutes to perform the offline training until reached the convergence.

Online Human Subject Testing Experiment

Experimental Protocol and Setup

The offline trained policy was implemented on the online able-bodied subject testing experiments. The male subject was the same one from whom we collected the offline training data. He was involved with informed consent. During the experiment, the subject wore a powered knee prosthesis and walked on a split-belt treadmill at a fixed speed of 0.6 m/s without holding handrails.

The entire experiment consisted of three sessions with different sets of initial impedance parameters for the prosthetic knee. The three sets of parameters were randomly selected, yet initially feasible to carry on policy iteration. The subject experienced 40 updates of the impedance control parameters for each phase of the FSM during a single experiment session. To reduce the influence of noises introduced by human variance during walking, the update period (i.e., the time index k in (5)) was set as 4 gait cycles (i.e., the states were obtained as an average of every 4 gait cycles). The proposed offline policy iteration based RL controller was used to automatically update impedance control parameters online such that actual knee kinematics approached predefined target points. At the beginning and at the end of each session, the subject had two stages of acclimation walking corresponding to the initial and final set of parameters, respectively. Each stage consisted of 20 gait cycles. The measured knee kinematics in the corresponding acclimation were averaged out to contrast the before-after effects of the proposed controller.

The robotic knee prosthesis used a slider-crank mechanism, where the knee motion was driven by the rotation of the moment arm powered by the DC motor through the ball screw. The prosthetic knee kinematics were recorded by a potentiometer embedded in the prosthesis. Some major gait events determining phase transitions in the finite state machine were detected by a load cell. The control system of the robotic knee prosthesis was implemented by LabVIEW and MATLAB in a desktop PC.

Performance Evaluations

Measures of knee kinematics were obtained at the beginning acclimation stage and at the ending acclimation stage during each session. These measurements reflect how the prosthetic knee joint moved when it interacted with the human subject before and after experiencing the control parameter update. By comparing the respective errors with respect to target points, the performance of the RL controller in a human-prosthesis system can be assessed.

While knee kinematic measures provide a quantitative evaluation of controller performance in terms of reaching desired gait target points, it is also necessary to consider an acceptable error range for the kinematic states. This is because the inherent human variance during walking. The experiments indicate that when the peak errors and duration errors are within 2 degrees and 2 percent range of the target values, respectively, the human subject would not feel any discomfort or insecure while walking. Therefore, in this study, those error bounds were adopted.

Experimental Results

Figures 15A, 15B, 15C:
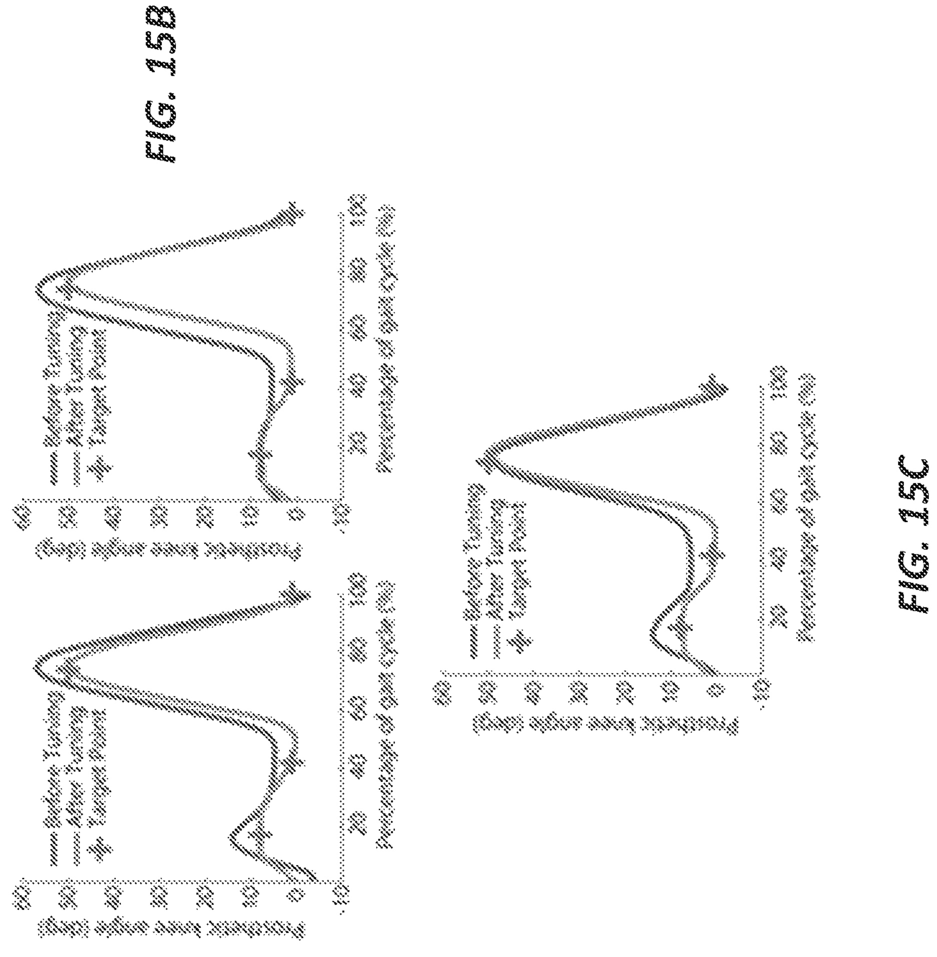
FIGS. 15A-15C are graphs illustrating three comparisons (corresponding to three different sets of initial impedance parameters) of knee kinematics for before and after impedance parameter tuning.
Figures 16A, 16B:
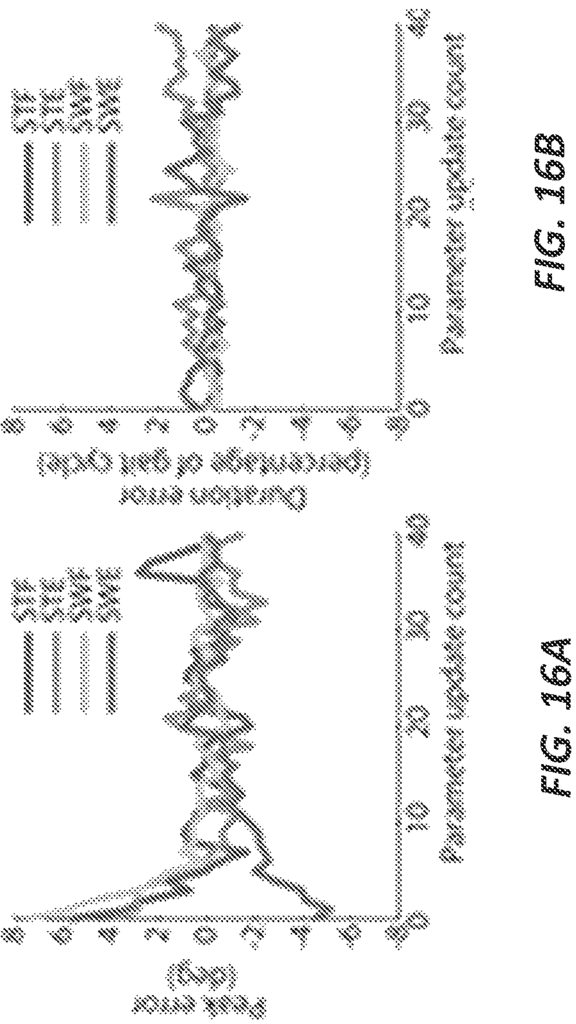
FIGS. 16A-16B are graphs illustrating the evolution of states ((FIG. 16A) peak error and (FIG. 16B) duration error) as impedance parameters were updated. This result corresponds to the case with the first set of initial parameters (i.e., the same initial condition as in FIG. 15A).
Figures 17A, 17B, 17C, 17D:
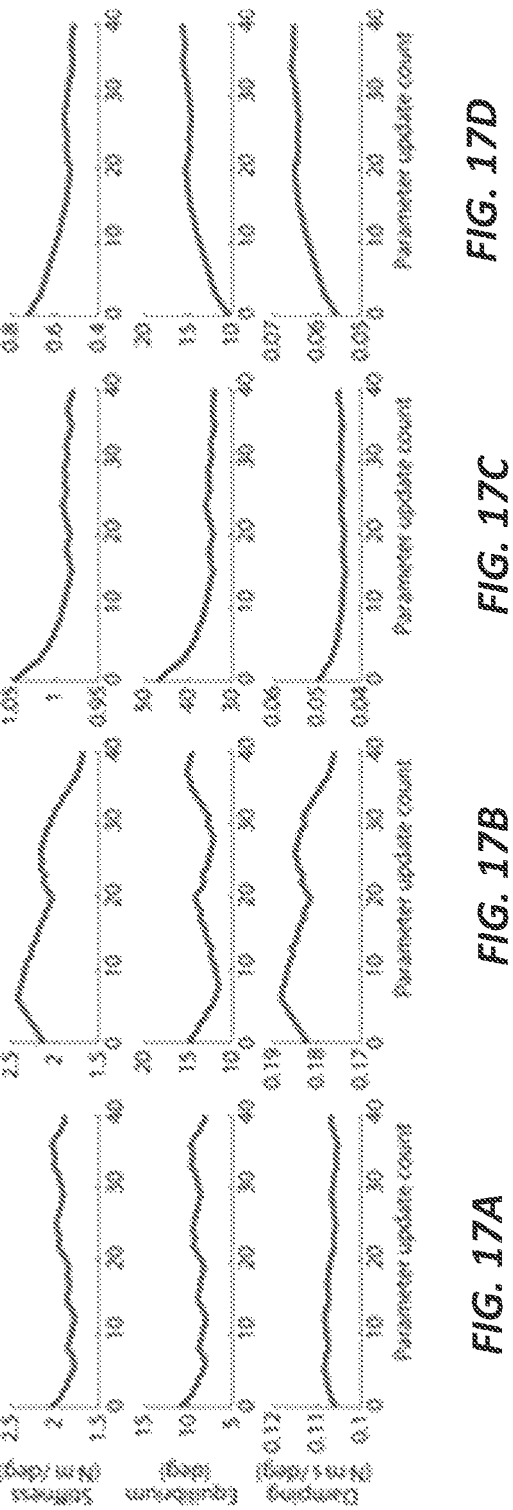
FIGS. 17A-17D are graphs illustrating the evolution of peak errors and duration errors during the experimental session under the first set of initial parameters corresponding to the first result in FIG. 15A. Since similar results were obtained from other experiment sessions, hereafter the result from the first session are only presented as an example. All four phases experienced reduction in the peak angles errors at the end. Specifically, the peak error decreased from 5.8 degrees to −0.2 degrees for STF, from 3.8 degrees to −1.5 degrees in the STE phase. For SWF and SWE, they dropped from 7.4 degrees to 0.18 degrees and from −4.4 degrees to 0.05 degrees respectively.

As FIGS. 15A-15C show, the knee kinematics of the initial acclimation stages were different in three different sessions and distant from the target points, especially the peak angle errors. Clearly, after the impedance parameters were adjusted by the proposed RL controller, knee kinematics of the final acclimation stages approached the target points. Specifically, the averaged absolute values of the peak errors over the three sessions deceased from 4.18±3.28 degrees to 0.56±0.47 degrees for STF, from 4.33±0.44 degrees to 1.11±0.66 degrees for STE, from 4.92±3.78 degrees to 0.14±0.04 degrees for SWF and from 3.21±1.23 degrees to 0.25±0.23 degrees for SWE. The results indicate that offline policy iteration based RL controller is able to reshape the prosthetic knee kinematics to meet the target points from different initial parameter settings.

The duration errors were insignificant, i.e., they were within the range of two percent of one gait cycle, and they remained within the range over the entire session. There are two considerations in this study. First, the duration time is controlled partially by human behavior, or in other words, the effect of controller on this state at the prosthetic knee is not the exclusively decisive factor. Second, given the previous consideration, we placed more emphasis on the peak error than the duration error as reflected in the weighting matrix $R_x$ in the quadratic cost measure.

The state errors at the final stage are mostly within the bounds of 2 degrees and 2 percent, respectively. These errors remained within bounds thereafter the first 10 parameter update cycles (40 gait cycles, about 1.3 minutes). Compared to the state errors achieved by dHDP as described herein, the offline policy iteration based RL controller achieved comparable performance with small errors (i.e. ±2 degrees, ±2 percent), but with less time to adjust the impedance control parameters. Specifically, it took dHDP 10 minutes of experiment (300 gait cycles) to achieve comparable state errors.

Note that the peak errors from the STF and the STE phases are usually associated with more oscillations than the other two swing phases as the state errors approach zeros (from the $10^{th}$ update to the $40^{th}$ update). In addition, as illustrated in FIGS. 17A-17D, the impedance parameters exhibited different change patterns during the experimental sessions. It is apparent that the impedance parameters during swing phases converged in the first 20 updates and remained stationary thereafter. However, the impedance parameters exhibited somewhat oscillatory patterns during the stance phases. It is actually not surprising when the different patterns are seen in the above. As can be understood, the stance phases involve direct interactions and thus directly affected by the ground, the human subject and the robotic prosthesis (for example, loading induced variation). Such varying interactions would introduce more perturbations to the prosthesis and result in oscillations. Whereas the swing phases are less likely to be affected by these factors and thus the state errors during these phases appear more stationary. Under the above discussed disturbances, the RL controller responded by making adjustments when it observed discrepancies between target and actual states. This unique phenomena is a result of dealing with an inherently co-adapting human-prosthesis system.

CONCLUSION

A data efficient and time efficient approximate policy iteration RL controller to optimally configure impedance parameters automatically for robotic knee prosthesis has been developed. The learning controller was trained offline using historical data and then the learned control policy was applied for online control of the prosthetic knee. The experimental results validated this approach and showed that it reproduced near-normal knee kinematics for the robotic knee prosthesis. The results proved that the offline policy iteration based RL controller is a promising new tool to solve the challenging parameter tuning problems for the robotic knee prosthesis with human in the loop.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A system comprising:

a powered prosthesis comprising:

a joint, a motor mechanically coupled to the joint, the motor being configured to drive the joint, a plurality of sensors configured to measure a plurality of gait parameters associated with a subject, a finite state machine configured to determine a gait cycle state of a plurality of gait cycle states based on the measured gait parameters, and an impedance controller configured to output a control signal for adjusting a torque of the motor, wherein the torque is adjusted as a function of the measured gait parameters and a plurality of impedance control parameters, wherein the impedance control parameters are dependent on the determined gait cycle state; and a reinforcement learning controller operably connected to the powered prosthesis, wherein the reinforcement learning controller is configured to tune at least one of the impedance control parameters to achieve a target gait characteristic using a training data set.

2. The system of claim 1, wherein the training data set comprises real-time data collected by the sensors while the subject is walking.

3. The system of claim 2, wherein the reinforcement learning controller is configured to tune the at least one of the impedance control parameters to achieve the target gait characteristic in about 300 gait cycles.

4. The system of claim 2, wherein the reinforcement learning controller is configured to tune the at least one of the impedance control parameters to achieve the target gait characteristic in about 10 minutes.

5. The system of claim 2, wherein the reinforcement learning controller is further configured to:

receive the measured gait parameters; and derive a state of the powered prosthesis based on the measured gait parameters, wherein the at least one of the impedance control parameters is tuned to achieve the target gait characteristic in response to the state of the powered prosthesis.

6. The system of claim 1, wherein the reinforcement learning controller comprises a plurality of direct heuristic dynamic programming (dHDP) blocks, each dHDP block being associated with one of the plurality of gait cycle states.

7. The system of claim 6, wherein each dHDP block comprises at least one neural network.

8. The system of claim 7, wherein each dHDP block comprises an action neural network (ANN) and a critic neural network (CNN).

9. The system of claim 1, wherein the training data set comprises offline training data.

10. The system of claim 9, wherein the reinforcement learning controller is configured to execute an approximate policy iteration.

11. The system of claim 9, wherein the training data set further comprises real-time data collected by the sensors while the subject is walking.

12. The system of claim 11, wherein the reinforcement learning controller is further configured to:

receive the measured gait parameters;

derive a state of the powered prosthesis based on the measured gait parameters; and refine the at least one of the impedance control parameters to achieve the target gait characteristic in response to the state of the powered prosthesis.

13. The system of claim 1, wherein the impedance control parameters include a respective set of impedance control parameters for each of the plurality of gait cycle states.

14. The system of claim 1, wherein the plurality of gait cycle states comprises a plurality of level ground walking gait cycle states.

15. The system of claim 14, wherein the level ground walking gait cycle states comprise stance flexion (STF), stance extension (STE), swing flexion (SWF), and swing extension (SWE).

16. The system of claim 1, wherein the impedance control parameters comprise at least one of a stiffness, an equilibrium position, or a damping coefficient.

17. The system of claim 1, wherein the target gait characteristic is a gait characteristic of a non-disabled subject.

18. The system of claim 1, wherein the measured gait parameters comprise at least one of a joint angle, a joint angular velocity, a ground reaction force, a duration of a gait cycle state, or a load applied to the joint.

19. The system of claim 1, wherein the joint is a prosthetic knee joint, a prosthetic ankle joint, or a prosthetic hip joint.

20. A method for tuning a powered prosthesis, the powered prosthesis comprising a joint, a motor mechanically coupled to the joint, a plurality of sensors, a finite state machine, and an impedance controller, the method comprising:

receiving a plurality of gait parameters associated with a subject from at least one of the sensors;

determining, using the finite state machine, a gait cycle state based on the received gait parameters;

training a reinforcement learning controller with a training data set to tune at least one of a plurality of impedance control parameters to achieve a target gait characteristic; and outputting, using the impedance controller, a control signal for adjusting a torque of the motor, wherein the torque is adjusted as a function of the measured gait parameters and the impedance control parameters, wherein the impedance control parameters are dependent on the gait cycle state.

21. The method of claim 20, wherein the training data set comprises real-time data received from the sensors while the subject is walking.

22. The method of claim 21, further comprising deriving a state of the powered prosthesis based on the received gait parameters, wherein the step of training the reinforcement learning controller comprises tuning the at least one of the impedance control parameters to achieve the target gait characteristic in response to the state of the powered prosthesis.

23. The method of claim 20, wherein the training data set comprises offline training data.

24. The method of claim 23, further comprising collecting the offline training data, wherein the step of training the reinforcement learning controller comprises tuning the at least one of the impedance control parameters to achieve the target gait characteristic based on the offline training data.

25. The method of claim 24, wherein the training data set further comprises real-time data received from the sensors while the subject is walking, the method further comprising deriving a state of the powered prosthesis based on the received gait parameters, wherein the step of training the reinforcement learning controller further comprises refining the at least one of the impedance control parameters to achieve the target gait characteristic in response to the state of the powered prosthesis.

* * * * *